(12) United States Patent
Taguchi et al.

(10) Patent No.: US 8,183,527 B2
(45) Date of Patent: May 22, 2012

(54) GAS DETECTING METHOD AND GAS DETECTING APPARATUS

(75) Inventors: Toshiyuki Taguchi, Okazaki (JP); Toshihiro Wakita, Aichi-gun (JP); Kiyomi Sakakibara, Iwakura (JP)

(73) Assignee: Kabushiki Kaisha Toyota Chuo Kenkyusho, Aichi (JP)

( * ) Notice: Subject to any disclaimer, the term of this patent is extended or adjusted under 35 U.S.C. 154(b) by 542 days.

(21) Appl. No.: 12/521,099

(22) PCT Filed: Dec. 21, 2007

(86) PCT No.: PCT/JP2007/074738
§ 371 (c)(1),
(2), (4) Date: Jun. 24, 2009

(87) PCT Pub. No.: WO2008/081757
PCT Pub. Date: Jul. 10, 2008

(65) Prior Publication Data
US 2010/0025585 A1  Feb. 4, 2010

(30) Foreign Application Priority Data

Dec. 28, 2006 (JP) .................................. 2006-355974
Aug. 7, 2007 (JP) .................................. 2007-205593

(51) Int. Cl.
*G01J 5/02* (2006.01)
*G01N 21/00* (2006.01)
(52) U.S. Cl. ................................ 250/339.13; 250/338.5
(58) Field of Classification Search ............. 250/339.13, 250/338.5
See application file for complete search history.

(56) References Cited

U.S. PATENT DOCUMENTS 5,070,245 A   12/1991  Rantala et al.
5,309,921 A * 5/1994  Kisner et al. .................. 600/532
5,531,225 A   7/1996  Nawata et al.
(Continued)

FOREIGN PATENT DOCUMENTS
JP         A-02-236441         9/1990
(Continued)

OTHER PUBLICATIONS

Aoki, "Pneumatic Infrared Detector", *Readout HORIBA Technical Reports*, vol. 7, Jul. 1993, p. 64.

*Primary Examiner* — David Porta
*Assistant Examiner* — Mindy Vu
(74) *Attorney, Agent, or Firm* — Oliff & Berridge, PLC

(57) ABSTRACT

A concentration of ethanol is detected without using any light source such as a lamp by utilizing a face of a human being as a light source. The gas detecting apparatus has an optical filter for ethanol which allows to transmit an infrared light having a predetermined wavelength band including an absorption spectrum derived from a C—O stretching vibration of ethanol contained in breath in an absorption spectrum generated by interaction with infrared light emitted from the face of a person, an optical filter for reference that allows to transmit an infrared light having a wavelength band emitted from the face of the person, a converting component for ethanol that converts the infrared light transmitted through the optical filter for ethanol to electric signals, a converting component for reference that converts an infrared light transmitted through the optical filter for reference to electric signals, and a detection component that detects the concentration of ethanol gas based on the electric signals converted by the converting component for ethanol and the electric signals converted by the converting component for reference.

16 Claims, 20 Drawing Sheets

U.S. PATENT DOCUMENTS

| | | | | |
|---|---|---|---|---|
| 5,770,793 | A * | 6/1998 | Stock | 73/23.21 |
| 5,793,043 | A | 8/1998 | Weckstrom et al. | |
| 5,971,937 | A | 10/1999 | Ekstrom | |
| 2007/0077176 | A1 | 4/2007 | Lambert et al. | |
| 2008/0236275 | A1 * | 10/2008 | Breed et al. | 73/290 V |

FOREIGN PATENT DOCUMENTS

| | | |
|---|---|---|
| JP | A-06-197897 | 7/1994 |
| JP | A-07-120463 | 5/1995 |
| JP | A-08-201286 | 8/1996 |
| JP | A-09-164130 | 6/1997 |
| JP | A-09-281039 | 10/1997 |
| JP | A-2000-230900 | 8/2000 |
| JP | A-2004-212217 | 7/2004 |
| JP | A-2004-279228 | 10/2004 |
| JP | A-2005-296252 | 10/2005 |
| JP | A-2007-147592 | 6/2007 |

* cited by examiner

FIRST EMBODIMENT

SECOND EMBODIMENT

THIRD EMBODIMENT

FOURTH EMBODIMENT

FIFTH EMBODIMENT $n_{cn}(t), n_{en}(t)$ $n_{cb}, n_{eb}$

MAGNIFICATION $\alpha(t)$ $n_{cm}, n_{em}$

EtOH SENSOR   $\Delta a$ $CO_2$ SENSOR   $\Delta c$

CONCENTRATION OF ALCOHOL $= \dfrac{\Delta a}{\Delta c} \cdot$ CONCENTRATION OF CARBON DIOXIDE

SIXTH EMBODIMENT

SEVENTH EMBODIMENT

EIGHTH EMBODIMENT

NINTH EMBODIMENT

FIG. 24
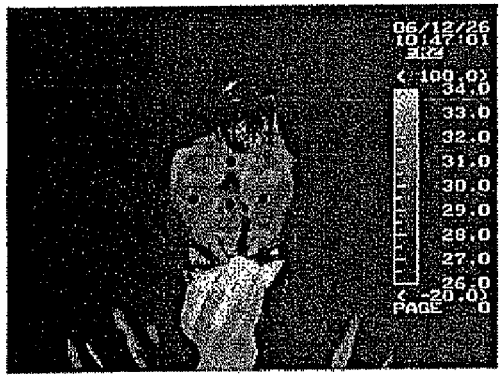 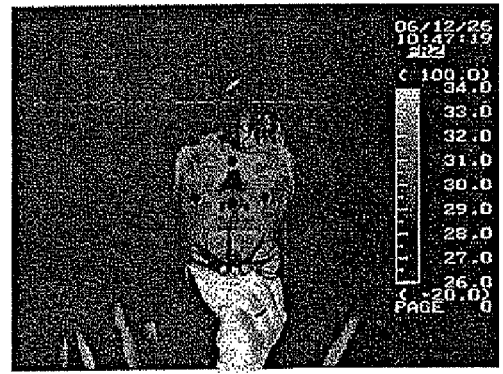
(1) GAS BAG: ATMOSPHERE    (2) GAS BAG: 2mg/ L ETHANOL

GAS DETECTING METHOD AND GAS DETECTING APPARATUS

TECHNICAL FIELD

The invention relates to a gas detecting method and a gas detecting apparatus, and more particularly to a gas detecting method and a gas detecting apparatus which may accurately detect an ethanol concentration from breath of a driver.

BACKGROUND ART

Conventionally, there are known an oxide semiconductor type, a fuel cell type, an infrared absorption type, a contact combustion type, and the like as detecting methods of ethanol contained in breath, and there are also proposed a technique for stopping start of an engine by detecting an ethanol concentration of a driver, and the like (Japanese Patent Application Laid-Open (JP-A) No. 2004-212217, JP-A No. 2004-279228, JP-A No. 2005-296252, JP-A No. H06-197897, JP-A No. 2007-147592).

Although a skin structure infrared light absorption method and the like are also proposed as a noninvasive measuring method of ethanol in blood, a time lag occurs until ethanol taken into a body reaches blood, from which a problem of a detection time lag arises.

Further, there is proposed a pneumatic infrared detecting apparatus as an accurate non-dispersive infrared analyzer making use of infrared absorption (Readout HORIBA Technical Reports No. 7 July 1993).

DISCLOSURE OF THE INVENTION

Problems to be Solved by the Invention

However, when an ethanol concentration is detected at a position away from a person to be checked, a problem arises in the conventional techniques in that since breath is arbitrarily diluted in atmosphere, a concentration of ethanol gas may not be accurately detected.

Further, in the conventional technique making use of the infrared absorption, a problem arises in that a light source such as an infrared lamp must be assembled to an apparatus.

A first object of the invention, which was made to solve the above problems, is to provide a gas detecting method and a gas detecting apparatus capable of accurately detecting an ethanol gas concentration even if breath is diluted in atmosphere.

Further, a second object of the invention is to provide a gas detecting method and a gas detecting apparatus capable of detecting an ethanol concentration making use of the face of a person as a light source without using a light source such as a lamp.

Means for Solving the Problem

To achieve the first object, a gas detecting method of the present invention detects the physical quantity relating to the concentration of ethanol gas as well as detects the physical quantity relating to the concentration of correction gas comprising oxygen and detects a physical quantity relating to the concentration of ethanol gas contained in breath based on the detected physical quantity relating to the concentration of correction gas and the detected physical quantity relating to the concentration of ethanol gas.

Further, a gas detecting apparatus of the invention is arranged by including ethanol detecting component for detecting a physical quantity relating to the concentration of ethanol gas, correction gas detecting component for detecting a physical quantity relating to the concentration of correction gas comprising oxygen, and concentration detecting component for detecting a physical quantity relating to the concentration of ethanol gas contained in breath based on the detected physical quantity relating to the concentration of correction gas and the detected physical quantity relating to the concentration of ethanol gas.

According to the gas detecting method and the gas detecting apparatus of the invention, since the physical quantity relating to the concentration of ethanol is detected as well as the physical quantity relating to the concentration of correction gas comprising oxygen is detected and the physical quantity relating to the concentration of ethanol gas contained in breath is detected based on the detected physical quantity relating to the concentration of correction gas and the detected physical quantity relating to the concentration of ethanol gas, even if breath is diluted in the atmosphere, the physical quantity relating to the ethanol concentration may be accurately detected.

An oxygen sensor for detecting the concentration of oxygen using a solid electrolyte may be used as a correction gas concentration detecting gas sensor that constitutes correction gas detecting component of the invention.

Advantages and disadvantages of correction gas (for example, vapor, carbon dioxide, or oxygen) used in the invention will be explained based on the following Table 1.

TABLE 1

|  | Vapor | Carbon dioxide | Oxygen |
|---|---|---|---|
| Concentration stability in atmosphere | Δ | ○ | ○ |
| Concentration stability in compartment | X | Δ | ○ |
| Correction by pressure sensor | necessary | necessary | may be replaced by oxygen sensor |

A vapor concentration is disadvantageous in that since the concentration is changed by humidity in the atmosphere which is changed by a peripheral temperature and rain, the concentration thereof in the atmosphere (base line) is not stabilized. In contrast, the concentration of carbon dioxide in the atmosphere is 0.04% and remains in changed. Likewise, the concentration of oxygen in the atmosphere is 21% and remains unchanged. Accordingly, carbon dioxide or oxygen is preferably used from the view point of stability of the concentration in the atmosphere.

Further, although the concentration of carbon dioxide in a compartment is unchanged when no occupant exists, it gradually increases when occupants exist. This is because the breath of people includes carbon dioxide about 100 times that of the atmosphere. Accordingly, although a problem is unlike to occur when a few people exist, when many people exist in a closed compartment, the base line of carbon dioxide may increase and not be stabilized. Further, when atmosphere is introduced by opening a window, the concentration of carbon dioxide decreases.

In contrast, the concentration of oxygen in the compartment is approximately unchanged regardless the number of people in a vehicle. Although the concentration of oxygen contained in breath of a person is about 16% which is about 5% lower than that contained in the atmosphere, the difference of oxygen between the person and the atmosphere is smaller than the difference of carbon dioxide therebetween. Thus, even if many people exist in a compartment for a long time, the concentration of oxygen in the compartment is not substantially different from that of the atmosphere.

The concentration of vapor changes according to the number of occupants in the compartment.

Therefore, carbon dioxide or oxygen is preferably used and oxygen is more preferably used from the view point of concentration stability in the compartment.

Further, since the atmospheric pressure becomes low at a location having a high altitude, a pressure correction is necessary to accurately calculate an alcohol concentration. Ordinarily, the pressure is detected by a pressure sensor and corrected by an alcohol concentration. In contrast, since the oxygen partial pressure in the atmosphere correlates with the atmospheric pressure, the pressure correction may be performed using an oxygen sensor in place of the pressure sensor.

Accordingly, when it is necessary to correct the pressure, it is preferable to use oxygen gas as correction gas.

From the reason described above, oxygen gas is used as the correction gas in the invention.

The gas detecting apparatus for detecting the physical quantity relating to the concentration of ethanol gas contained in breath subjected to an atmospheric pressure correction has ethanol detecting component for detecting a physical quantity relating the concentration of ethanol gas, correction gas detecting component for detecting a physical quantity relating to the concentration of correction gas comprising oxygen, correction gas detecting component for detecting the physical quantity relating to the concentration of correction gas comprising oxygen, and concentration detecting component for detecting the physical quantity relating to the concentration of ethanol gas contained in breath subjected to the atmospheric pressure correction based on the detected concentration of the correction gas based on the detected physical quantity relating to the concentration of correction gas and on the physical quantity relating to the concentration of ethanol gas.

The gas detecting method of detecting the physical quantity relating to the concentration of ethanol gas contained in breath subjected to an atmospheric pressure correction may detect the physical quantity relating to the concentration of ethanol gas as well as detect the physical quantity relating to the concentration of correction gas comprising oxygen and may detect the physical quantity relating to the concentration of ethanol gas contained in breath subjected to the atmospheric pressure correction based on the detected concentration of correction gas based on the detected physical quantity relating to the concentration of correction gas and the physical quantity relating to the concentration of ethanol gas.

Note that since vapor or carbon dioxide may be also used as the correction gas, vapor or carbon dioxide is used as the correction gas or at least one type of gas of vapor, carbon dioxide, and oxygen is used as the correction gas in the invention explained below.

A gas detecting apparatus of the invention using at least one type of gas of vapor, carbon dioxide, and oxygen has ethanol detecting component for detecting a physical quantity relating to the concentration of ethanol gas, correction gas detecting component for detecting the physical quantity relating to the concentration of correction gas comprising at least one type of gas of vapor, carbon dioxide, and oxygen a breath filter for allowing the transmission of a breath frequency component from the detected physical quantity relating to the concentration of correction gas or from the detected physical quantity relating to the concentration of correction gas and the detected physical quantity relating to the concentration of ethanol gas, and concentration detecting component for detecting the physical quantity relating to the concentration of ethanol gas contained in breath based on the physical quantity relating to the concentration of correction gas transmitted through the breath filter and the physical quantity relating to the concentration of ethanol gas detected by the ethanol detecting component or based on the physical quantity relating to the concentration of correction gas transmitted through the breath filter and the physical quantity relating to the concentration of ethanol gas transmitted through the breath filter.

Since the invention uses a breath filter comprising, for example, a high-pass filter to be described later, which allows the transmission of the signal of a breath frequency component, the physical quantity relating to the concentration of ethanol may be accurately detected even when a detected signal varies according to a breath cycle.

The correction gas detecting component of the invention may comprise carbon dioxide detecting component having an optical filter for carbon dioxide, which allows the transmission of an infrared light having a predetermined wavelength including an absorption spectrum derived from a C—O stretching vibration of carbon dioxide in an absorption spectrum generated by interaction with infrared light emitted from the face of a person and carbon dioxide converting component for converting the infrared light transmitted through the optical filter for carbon dioxide to an electric signal, vapor detecting component having an optical filter for vapor, which allows the transmission of an infrared light having a predetermined wavelength including an absorption spectrum in an absorption spectrum generated by interaction with infrared light emitted from the face of a person generated by vapor, and converting component for vapor for converting the infrared light transmitted through the optical filter for vapor to an electric signal, and a gas sensor for detecting the physical quantity relating to the concentration of correction gas comprising at least one type of gas of vapor, carbon dioxide, and oxygen, a vapor sensor comprising a light source for emitting an infrared light and an infrared light detector, or a carbon dioxide sensor comprising a light source for emitting an infrared light and an infrared light detector.

A vapor sensor for detecting the concentration of vapor using an oxide semiconductor or a polymer film capacitance, a carbon dioxide sensor for detecting the concentration of carbon dioxide using a solid electrolyte, or an oxygen sensor for detecting the concentration of oxygen using a solid electrolyte may be used as a gas sensor for detecting the concentration of correction gas.

A light source using a semiconductor laser, a blackbody furnace, a ceramic heater, or the like may be used as a light source for emitting an infrared light, and a bolometer, an SOI diode, a thermopile, or a ferroelectric detector may be used as an infrared light detector.

When the physical quantity relating to the concentration of vapor is detected using an infrared light, the gas detecting apparatus may comprise ethanol detecting component for detecting the physical quantity relating to the concentration of ethanol gas, vapor detecting component having an optical filter for vapor, which allows the transmission of an infrared light having a predetermined wavelength including an absorption spectrum in an absorption spectrum generated by interaction with infrared light emitted from the face of a person generated by vapor, and converting component for vapor for converting the infrared light transmitted through the optical filter for vapor to an electric signal, or correction gas detecting component comprising a vapor sensor having a light source for emitting an infrared light and an infrared light detector for detecting the physical quantity relating to the concentration of vapor as the physical quantity relating to the concentration of correction gas, and concentration detecting component for detecting the physical quantity relating to the concentration of ethanol gas in breath based on the detected physical quantity relating to the concentration of correction gas and the detected physical quantity relating to the concentration of ethanol gas.

Further, the ethanol detecting component of the respective inventions explained above may comprise an alcohol sensor which comprises an ethanol detector having an optical filter for ethanol, which allows the transmission of an infrared light having a predetermined wavelength band including an absorption spectrum derived from a C—O stretching vibration of ethanol in an absorption spectrum generated by interaction with infrared light emitted from the face of a person, and converting component for ethanol for converting the infrared light transmitted through the optical filter for ethanol to an electric signal, and a gas sensor for detecting the physical quantity relating to the concentration of ethanol gas using an oxide semiconductor, or a light source for emitting an infrared light and an infrared light detector.

A light source using a semiconductor laser, a blackbody furnace, a ceramic heater, or the like may be used as a light source for emitting an infrared light of an alcohol sensor likewise the above mentioned, and a bolometer, an SOI diode, a thermopile, or a ferroelectric detector may be used as an infrared light detector likewise the above mentioned.

Then, concentration detecting component of the respective inventions may detect the concentration of ethanol gas contained in breath or a value proportional to the concentration as the physical quantity relating to the concentration according to any one of the following expressions (1) to (4).

physical quantity relating to the concentration of ethanol gas=$(\Delta a/\Delta b)$ (1)

physical quantity relating to the concentration of ethanol gas=$(\Delta a/\Delta b) \cdot BG$ (2)

physical quantity relating to the concentration of ethanol gas=$(\Delta a/\Delta b) \cdot (BG-AG)+$[EtOH]base (3)

physical quantity relating to the concentration of ethanol gas=$\Delta a \cdot Di+$[EtOH]base (4)

where, $\Delta a$ shows the amount of change, the rate of change, or the integration value in a predetermined time of the physical quantity relating to the concentration of ethanol gas detected by the ethanol detecting component, $\Delta b$ shows the amount of change, the rate of change, or the integration value in a predetermined time of the physical quantity relating to the concentration of correction gas detected by the correction gas detecting component, BG shows the physical quantity relating to the predetermined concentration of correction gas in breath, AG shows the physical quantity relating to the concentration of correction gas in the atmosphere detected by correction gas detecting component, [EtOH]base shows the physical quantity relating to the concentration of ethanol gas in the atmosphere detected by the ethanol detecting component, and Di shows a breath dilution magnification shown by the following expression.

$Di=(BG-AG)\Delta b$ (5)

When the expressions (1) and (2) are used, the physical quantity relating to the concentration of ethanol gas may be accurately detected when the amount of breath is sufficiently small to the atmosphere.

Further, since the expressions (3) and (4) take the amount of breath to the atmosphere into consideration, the physical quantity relating to the concentration of ethanol gas may be accurately detected not only when breath is diluted but also when breath comes into direct contact with the detecting component without being diluted.

A gas detecting method of the invention for achieving the second object has a feature in that the intensity of an infrared light having a predetermined wavelength band including an absorption spectrum derived from a C—O stretching vibration of ethanol in an absorption spectrum generated by interaction with infrared light emitted from the face of a person is detected as an infrared light absorption intensity of ethanol, and the physical quantity relating to the concentration of ethanol gas contained in breath is detected based on the magnitude of the detected infrared light absorption intensity of ethanol The inventors of the invention have achieved the invention by using an infrared light emitted from the face of a person, which is used as light source, paying attention to the following points. The peak values of the infrared light emitted from the face of a person are 9.66 μm at 27° C. and 9.35 μm at 37° C. and are within approximately the same wavelength band as the central wavelength 9.5 μm of an absorption spectrum derived from a C—O stretching vibration of ethanol. Since the direction in which an infrared light is emitted from the face of a person is the same as the direction in which breath is blown out, ethanol gas contained in breath interacts with the infrared light emitted from the face of a person.

As a result, in the invention, the face of a person is used as a light source, and an infrared light having, for example, a predetermined wavelength band including an absorption spectrum derived from a C—O stretching vibration of ethanol contained in breath in an absorption spectrum generated by interaction with infrared light emitted from the face of the person is extracted and an infrared light having a predetermined wavelength band with the absorption spectrum as its central wavelength is preferably extracted, and the physical quantity relating to the concentration of ethanol gas contained in breath is detected from the intensity of the infrared light.

In the invention, since the face of a person is used as a light source, the physical quantity relating to the concentration of ethanol contained in breath may be accurately detected without using a light source such as an infrared lamp.

In the invention, the intensity of an infrared light, which has a predetermined wavelength band including an absorption spectrum derived from a C—O stretching vibration of ethanol in an absorption spectrum generated by interaction with infrared light emitted from the face of a person, is detected as an infrared light absorption intensity of ethanol as well as the intensity of an infrared light, which has a predetermined wavelength band including an absorption spectrum derived from a C—O stretching vibration of carbon dioxide in an absorption spectrum generated by interaction with infrared light emitted from the face of the person, is detected as an infrared light absorption intensity of carbon dioxide, and the physical quantity relating to the concentration of ethanol gas contained in breath is detected based on the detected infrared light absorption intensity of carbon dioxide and the detected infrared light absorption intensity of ethanol.

Since a person breathes, the concentration of ethanol contained in breath periodically changes according to breath rhythm. Further, when breath is collected at a position away from the mouth of a people since the concentration of ethanol contained in breath at the collecting position changes according to the breath rhythm as well as ethanol is detected as noise when ethanol is contained in the atmosphere, the concentration of ethanol may not be accurately detected. In the invention, the physical quantity relating to the concentration of ethanol gas contained in breath is detected based on a detected infrared light absorption intensity of carbon dioxide and a detected infrared light absorption intensity of ethanol, for example, based on the magnitude of the detected infrared light absorption intensity of ethanol to the detected infrared light absorption intensity of carbon dioxide paying attention to that the concentration of carbon dioxide in the atmosphere changes sufficiently slower than breath rhythm.

As a result, even when the concentration of ethanol gas is varied by breath, breath is diluted, or breath is collected at a position away from the mouth of a person, the physical quantity relating to the concentration of ethanol gas contained in breath may be accurately detected.

When ethanol is contained in breath, the concentration of ethanol and carbon dioxide exhausted to the atmosphere vary according to breath rhythm. In comparison with the above-mentioned, it may be assumed that the concentrations of ethanol and carbon dioxide, which originally exist in the atmosphere, vary sufficiently slower than breath rhythm. Accordingly, to prevent a noise component from being included in a detected signal of the concentration of ethanol gas contained in breath, a breath filter, which comprises a high-pass filter for allowing the transmission of the signal of a breath frequency component, may be used as described later. In this case, when the detected signal (second signal) of the physical quantity relating to the concentration of carbon dioxide, or both the detected signal (first signal) of the physical quantity relating to the concentration of ethanol gas and the detected signal (second signal) of the physical quantity relating to the concentration of carbon dioxide are transmitted through the breath filter, the physical quantity relating to the concentration of ethanol gas may be detected based on the first signal and the second signal transmitted through the breath filter or based on the second signal transmitted through the breath filter and the first signal transmitted through the breath filter, that is, based on, for example, the magnitude of the first signal to the second signal transmitted through the breath filter or based on the magnitude of the first signal transmitted through the breath filter to the second signal transmitted through the breath filter.

When breath is collected at a position away from the mouth of a people since vapor contained in breath of a person also has the feature explained above likewise carbon dioxide, the physical quantity relating to the concentration of ethanol gas contained in breath may be also accurately detected as described below using vapor in place of carbon dioxide.

More specifically, the intensity of an infrared light, which has a predetermined wavelength band including an absorption spectrum derived from a C—O stretching vibration of ethanol in an absorption spectrum generated by interaction with infrared light emitted from the face of a person, may be detected as an infrared light absorption intensity of ethanol as well as the intensity of an infrared light, which has a predetermined wavelength band including an absorption spectrum of vapor in an absorption spectrum generated by interaction with infrared light emitted from the face of the person, may be detected as an infrared light absorption intensity of vapor, and the physical quantity relating to the concentration of ethanol gas contained in breath may be detected based on the detected infrared light absorption intensity of vapor and the detected infrared light intensity of ethanol, for example, based on the magnitude of the detected infrared light absorption intensity of ethanol to the detected infrared light absorption intensity of vapor.

When an infrared light absorption intensity of vapor is detected, the physical quantity relating to the concentration of ethanol gas contained in breath may be also detected likewise the above-mention using the breath filter explained above.

The gas detecting apparatus of the invention may comprise an optical filter for ethanol, which allows the transmission of an infrared light having a predetermined wavelength band including an absorption spectrum derived from a C—O stretching vibration of ethanol in an absorption spectrum generated by interaction with infrared light emitted from the face of a person, converting component for ethanol for converting the infrared light transmitted through the optical filter for ethanol to an electric signal, and detecting component for detecting the physical quantity relating to the concentration of ethanol gas contained in breath based on the magnitude of the electric signal converted by the converting component for ethanol.

According to the gas detecting apparatus, the physical quantity relating to the concentration of ethanol contained in breath may be accurately detected using the face of a person as a light source without using a light source such as an infrared lamp as explained above.

The detecting component may detect the physical quantity relating to the concentration of ethanol gas [EtOH] according to the following expression.

$$[EtOH] = -\ln(Te/To)/ke \cdot L \qquad (6)$$

where, Te shows the amount of transmitted infrared light obtained from the electric signal converted by the converting component for ethanol, To shows the amount of infrared light emitted from the face of a person, ke shows an absorption coefficient of ethanol gas, L shows the interacting length between ethanol gas and the infrared light emitted from the face of the person, and ln shows natural logarithm.

Further, the gas detecting apparatus of the invention may comprise an optical filter for ethanol, which allows the transmission of an infrared light having a predetermined wavelength band including an absorption spectrum derived from a C—O stretching vibration of ethanol in an absorption spectrum generated by interaction with infrared light emitted from the face of a person, and converting component for ethanol for converting the infrared light transmitted through the optical filter for ethanol to an electric signal, converting component for ethanol for converting the infrared light transmitted through the optical filter for ethanol to an electric signal, converting component for reference for converting the infrared light transmitted through the optical filter for reference to an electric signal, converting component for reference for converting the infrared light transmitted through the optical filter for reference to an electric signal, and detecting component for detecting the physical quantity relating to the concentration of ethanol gas contained in breath based on the electric signals converted by the converting component for ethanol and the converting component for reference.

According to the gas detecting apparatus, since the amount of transmitted infrared light, which includes the wavelength band of the infrared light emitted from the face of a person as well as has a band excluding the predetermined wavelength band, is used, the physical quantity relating to the concentration of ethanol in breath may be accurately detected even when the amount of the infrared light emitted from the face of the person varies.

The detecting component of the gas detecting apparatus may detect the physical quantity [EtOH] relating to the concentration of ethanol gas according to the following expression.

$$[EtOH] = -\ln(Te/To)/ke \cdot L \qquad (7)$$

where, Te shows the amount of transmitted infrared light obtained from the electric signal converted by the conversion means for ethanol, To shows the amount of transmitted infrared light emitted from the face of a person obtained by the electric signal converted by the conversion means for reference, ke shows an absorption coefficient of ethanol gas, L shows the interacting length between ethanol gas and the infrared light emitted from the face of the person, and In shows natural logarithm.

Further, the gas detecting apparatus of the invention may comprise an optical filter for ethanol for allowing the transmission of an infrared light having a predetermined wavelength band including an absorption spectrum derived from a C—O stretching vibration of ethanol in an absorption spectrum generated by interaction with infrared light emitted from the face of a person; an optical filter for carbon dioxide for allowing the transmission of an infrared light having a predetermined wavelength band including an absorption spectrum derived from a C—O stretching vibration of carbon dioxide in an absorption spectrum generated by interaction with infrared light emitted from the face of the person; converting component for ethanol for converting the infrared light transmitted through the optical filter for ethanol to an electric signal; converting component for carbon dioxide for converting the infrared light transmitted through the optical filter for carbon dioxide to an electric signal; and detecting component for detecting the physical quantity relating to the concentration of ethanol gas contained in breath based on the electric signals converted by the converting component for carbon dioxide and the converting component for ethanol.

According to the gas detecting apparatus, the face of a person is used as the light source as well as attention is paid to that the concentration of carbon dioxide in the atmosphere changes sufficiently slower than breath rhythm. Thus, since the physical quantity relating to the concentration of ethanol gas is detected based on the magnitude of the infrared light absorption intensity of ethanol to the detected infrared light absorption intensity of carbon dioxide, even when breath is collected at a position away from the mouth of a person, the physical quantity relating to the concentration of ethanol gas contained in breath may be accurately detected.

The detecting component of the gas detecting apparatus may detect the physical quantity [EtOH] relating to the concentration of ethanol gas contained in breath based on the magnitude of the electric signal converted by the converting component for ethanol to the electric signal converted by the converting component for carbon dioxide according to the following expression for detecting the physical quantity relating to the concentration of ethanol gas contained in the breath.

$$[EtOH] = (ne(t_2) - ne(t_1))/(nc(t_2) - nc(t_1)) \qquad (8)$$

where, $ne(t_2)$, $ne(t_1)$ show the physical quantities relating to the concentration of ethanol gas shown by ne of the following expression at times $t_2$, $t_1$, and $nc(t_2)$, $nc(t_1)$ show the physical quantities relating to the concentration of carbon dioxide shown by no of the following expression at the times $t_2$, $t_1$.

$$ne = -\ln(Te/To)/ke \cdot L$$

$$nc = -\ln(Tc/To)/kc \cdot L$$

where, Te shows the amount of transmitted infrared light obtained from the electric signal converted by the converting component for ethanol, Te shows the amount of transmitted infrared light obtained from the electric signal converted by the converting component for carbon dioxide, To shows the amount of infrared light emitted from the face of a person, ke shows an absorption coefficient of ethanol gas, kc shows an absorption coefficient of carbon dioxide, and L shows the interacting length between ethanol gas and carbon dioxide and the infrared light emitted from the face of the person.

Further, since carbon dioxide contained in breath and vapor contained in breath have the same characteristics, the detection apparatus may comprise an optical filter for ethanol, which allowing the transmission of an infrared light having a predetermined wavelength band including an absorption spectrum derived from a C—O stretching vibration of ethanol in an absorption spectrum generated by interaction with infrared light emitted from the face of a person, an optical filter for vapor for allowing the transmission of an infrared light having a predetermined wavelength band including an absorption spectrum of vapor in an absorption spectrum generated by interaction with infrared light emitted from the face of a person, converting component for ethanol for converting the infrared light transmitted through the optical filter for ethanol to an electric signal, converting component for vapor for converting the infrared light transmitted through the optical filter for vapor to an electric signal; and detecting component for detecting the physical quantity relating to the concentration of ethanol gas contained in breath based on the electric signals converted by the converting component for vapor and the converting component for ethanol In this case, the detecting component may detect the physical quantity [EtOH] relating to the concentration of ethanol gas contained in breath based on the magnitude of the electric signal converted by the converting component for ethanol to the electric signal converted by the converting component for vapor according to the following expression for detecting the physical quantity relating to the concentration of ethanol gas contained in the breath.

$$[EtOH] = (ne(t_2) - ne(t_1))/(nw(t_2) - nw(t_1)) \qquad (9)$$

where, $ne(t_2)$, $ne(t_1)$ show the physical quantities relating to the concentration of ethanol gas shown by ne of the following expression at times $t_2$, ti, and $nw(t_2)$, $nw(v)$ show the physical quantity relating to the concentration of vapor shown by nw of the following expression at the times $t_2$, $t_1$.

$$ne = -\ln(Te/To)/ke \cdot L$$

$$nw = -\ln(Tw/To)/kw \cdot L$$

where, Te shows the amount of transmitted infrared light obtained from the electric signal converted by the converting component for ethanol, Tw shows the amount of transmitted infrared light obtained from the electric signal converted by the converting component for vapor, To shows the amount of infrared light emitted from the face of a person, ke shows an absorption coefficient of ethanol gas, kw shows an absorption coefficient of vapor, and L shows the interacting length between ethanol gas and vapor and the infrared light emitted from the face of the person.

Note that the expressions (8) and expression (9) correspond to the expression (1).

A gas detecting apparatus, which uses the physical quantities relating to the concentration of carbon dioxide or the physical quantity relating to the concentration of vapor, may be further provided with an optical filter for reference including the wavelength band of infrared light emitted from the face of a person as well as transmitting the infrared light having a band other than the predetermined wavelength band, and converting component for reference for converting the infrared light transmitted through the optical filter for reference to an electric signal, wherein the detecting component may detect the physical quantity relating to the concentration of ethanol gas further using the electric signal converted by the converting component for reference.

The gas detecting apparatus may be further provided with an optical filter for reference including the wavelength band of infrared light emitted from the face of a person as well as transmitting the infrared light having a band other than the predetermined wavelength band and converting component for reference for converting the infrared light transmitted through the optical filter for reference to an electric signal, wherein the detecting component may detect the physical quantity [EtOH] relating to the concentration of ethanol gas using the amount of transmitted light emitted from the face of the person obtained by the electric signal converted by the converting component for reference as the amount of infrared light To emitted from the face of the person.

The gas detecting apparatus explained above may be arranged such that it is further provided with a breath filter for allowing the transmission of the signal of a breath frequency component from the electric signal converted by the converting component for ethanol, and the detecting component detects the physical quantity relating to the concentration of ethanol gas based on the magnitude of the electric signal converted by the converting component for ethanol and transmitted through the breath filter.

The physical quantity relating to the concentration of ethanol may be accurately detected by providing the breath filter for allowing the transmission of the signal of the breath frequency component from the electric signal and detecting the physical quantity relating to the concentration of ethanol gas based on the magnitude of the electric signal transmitted through the breath filter even in a case in which the physical quantity relating to the concentration of ethanol contained in breath changes at a collecting position according to breath rhythm.

The breath filter may allow the transmission of not only the electric signal converted by the converting component for ethanol but also the signals of the breath frequency components from the electric signals converted by the converting component for ethanol and the electric signals converted by the converting component for carbon dioxide and may allows the transmission of the signals of the breath frequency components from the electric signals converted by the converting component for ethanol and the converting component for vapor Although the physical quantities relating to the concentrations of carbon dioxide and vapor contained in breath may change at the collecting position according to breath rhythm, the physical quantity relating to the concentration of ethanol may be accurately detected by providing the breath filter for allowing the transmission of the signal of the breath frequency component from the electric signal as described above.

A concentration or a value proportional to the concentration may be used as the physical quantity relating to the concentration of inventions described above. Further, although the breath filter allows the transmission of the signal of the breath frequency component, it may allow the transmission of only the signal of the breath frequency component.

Effect of the Invention

As described above, according to the invention, the physical quantity relating to the concentration of ethanol is detected as well as the concentration of ethanol gas contained in breath is detected using the concentration of correction gas comprising carbon dioxide or oxygen contained in breath or the concentration of correction gas comprising at least one type of gas of vapor, carbon dioxide, and oxygen as a reference. As a result, there can be obtained an advantage in that the physical quantity relating to the concentration of ethanol contained in breath may be accurately detected even when breath is diluted or a component in the atmosphere is mixed as noise.

Further, the face of a person is used as the light source, and an infrared light having a predetermined wavelength band including an absorption spectrum derived from the C—O stretching vibration of ethanol contained in breath in an absorption spectrum generated by interaction with infrared light emitted from the face of the person is extracted, and the physical quantity relating to the concentration of ethanol gas is detected from the intensity of the infrared light. As a result, there can be obtained an advantage in that the physical quantity relating to the concentration of ethanol contained in breath may be accurately detected without using a light source such as an infrared lamp.

BRIEF DESCRIPTION OF THE DRAWING

FIG. 24 is schematic views showing images picked up by the far infrared camera.

Figure 1:
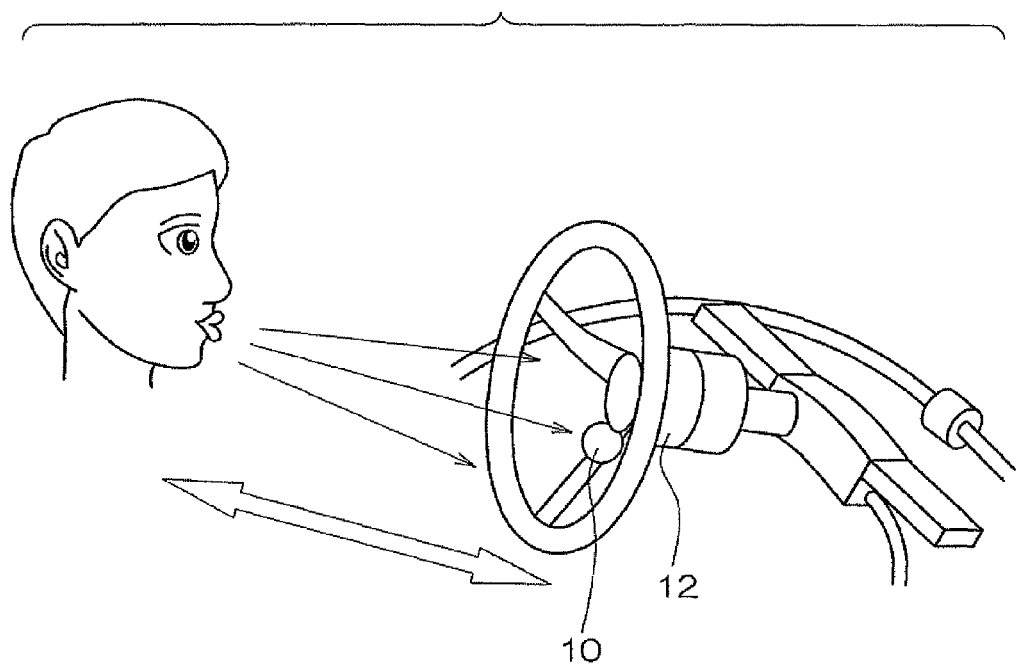
FIG. 1 is a schematic view showing an ethanol concentration detector of an exemplary embodiment in a state that it is attached to a steering column of a driver's compartment.

DESCRIPTION OF REFERENCE NUMERALS 10 ethanol concentration detector
12 steering column
20 optical filter for ethanol
22 photoelectric conversion device for ethanol
24 ethanol concentration determinator
30 optical filter for reference
32 photoelectric conversion device for reference
34 36 38 breath signal filter
40 optical filter for carbon dioxide
42 photoelectric conversion device for carbon dioxide
50 optical filter for vapor
52 photoelectric conversion device for vapor

BEST MODE FOR CARRYING OUT THE INVENTION

An exemplary embodiment of the invention will be explained below in detail referring to the drawings. Although the exemplary embodiment explained below will explain a case in which a concentration is used as a physical quantity relating to a concentration, it may be also explained likewise in a case in which a value proportional to a concentration is used.

As shown in FIG. 1, the exemplary embodiment is arranged such that an ethanol concentration detector 10 is attached to a steering column 12 disposed in a driver's compartment at a position at which the detector may receive an infrared light emitted from the face of a driver as well as to which breath of the driver may reach so that ethanol as one type of alcohols from the breath of the driver may be detected.

Figure 2:
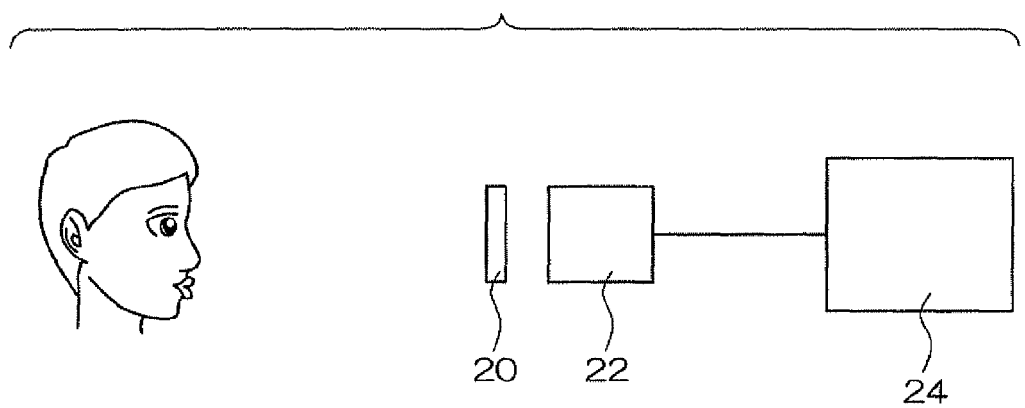
FIG. 2 is a schematic view showing a first exemplary embodiment of the invention.

Exemplary embodiments of the ethanol concentration detector as a gas detecting apparatus will be explained below. As shown in FIG. 2, an ethanol concentration detector 10 of a first exemplary embodiment has an optical filter 20 and a photoelectric conversion device 22 for ethanol. The optical filter 20 comprises a band-pass filter and allows the transmission an infrared light having a predetermined wavelength band (for example, a wavelength band of 9 μm to 10 μm having an absorption spectrum derived from a C—O stretching vibration of ethanol as its central wavelength) including an absorption spectrum (wavelength 9.5 μm) derived from the C—O stretching vibration of ethanol. The photoelectric conversion device 22 for ethanol comprises a bolometer, an SOI diode, a thermopile, or the like which converts the infrared light transmitted through the optical filter 20 to an electric signal and outputs an electric signal according to the amount of a transmitted light.

The photoelectric conversion device 22 for ethanol has an ethanol concentration determinator 24 connected thereto so that the ethanol concentration determinate 24 detects an ethanol gas concentration, compares a detected ethanol concentration with a threshold value, and determines an ethanol concentration. The ethanol concentration determinate 24 may comprise a microcomputer.

Figure 18:
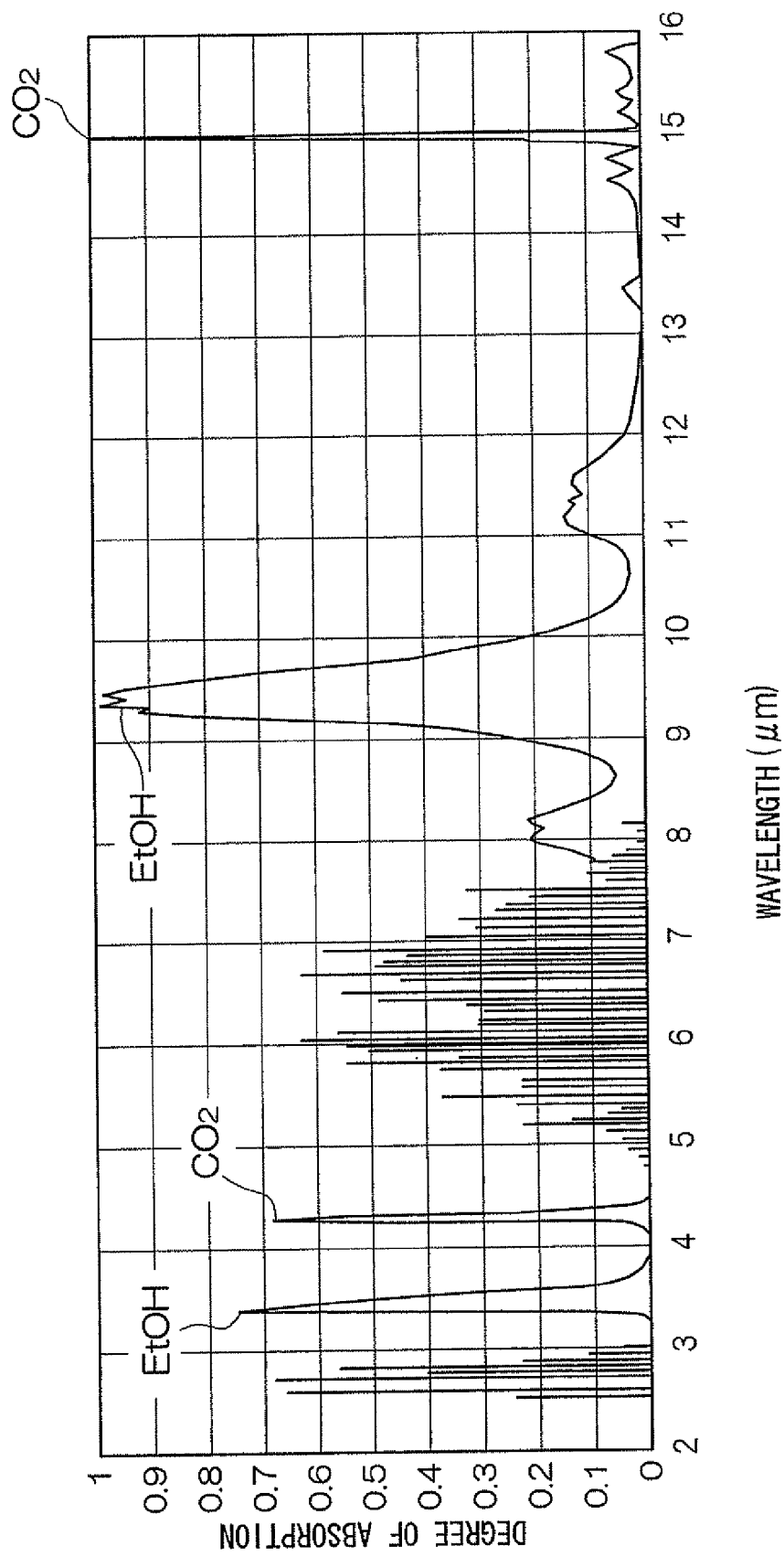
FIG. 18 is a graph showing a degree of absorption to the wavelengths ethanol and carbon dioxide.

The wavelength band of the infrared light emitted from the face of a person is about 2 μm to 100 μm at a temperature of 300° K., and the emitted intensity of the infrared light is maximized in the wavelength of about 9.5 μm. In contrast, as shown in FIG. 18, the central wavelength of the absorption spectrum derived from the C—O stretching vibration of ethanol is about 9.5 μm which is approximately the same as the central wavelength of the absorption spectrum derived from the C—O stretching vibration of ethanol in which the emitted intensity of the infrared light emitted from the face of the person is maximized.

Further, since the direction of the infrared light emitted from the face of the driver is the same as the direction in which breath is blown out, the ethanol gas in the breath interacts with the infrared light emitted from the face of the driver between the face of the driver and the ethanol concentration detector.

Therefore, according to the ethanol concentration detector of the exemplary embodiment, since the absorption spectrum is derived from the C—O stretching vibration of ethanol by the interaction between the infrared light emitted from the face of the driver and the ethanol in the breath, the intensity of an infrared light having a predetermined wavelength band including the absorption spectrum is lowered.

The intensity Te of the electric signal output from the photoelectric conversion device 22 for ethanol, ire., the amount of infrared light transmitted through the filter 20 is shown by an expression shown below.

$$Te = To \text{EXP}(-ne \cdot ke \cdot L) \tag{10}$$

where, T shows the amount of light of the face of a driver as a light source, ne shows an ethanol gas concentration, ke shows an absorption coefficient of the ethanol gas, L shows the interacting length (light path length shown by the distance from the optical filter 20 to the face of the driver) between gas and light, and EXP shows an exponent function.

The concentration [EtOH] of ethanol contained in breath is shown by an expression (11) shown below from the expression (10).

$$[EtOH] = ne = -\ln(Te/To)/ke \cdot L \tag{11}$$

where, ln shows natural logarithm.

Accordingly, the ethanol concentration determinator 24 calculates the ethanol concentration [EtOH] in breath according to the expression (11) and compares a calculated value with a predetermined threshold value, and when the calculated value is the threshold value or more, the ethanol concentration determinator 24 determines that the ethanol concentration is high and performs a control for preventing an unauthorized action by making it impossible to start an engine.

Note that it is sufficient to use, as the amount of light To of a light source, the average value of the previously detected amounts of light of a plurality of persons to be checked or a value which is obtained by detecting the infrared light emitted from the face of a driver before an ethanol concentration is detected by the photoelectric conversion device 22 without causing the infrared light to transmit through the optical filter 20. Since the amount of light To of the light source changes according to a time zone and a season, the amount of light To of the light source may be made change according to a time zone and a season.

According to the ethanol concentration detector of the exemplary embodiment, the intensity of the infrared light having the predetermined wavelength band including the absorption spectrum derived from the C—O stretching vibration of ethanol contained in breath generated by interaction with infrared light emitted from the face of a driver, is detected as an infrared light absorption intensity of the ethanol, and an ethanol gas concentration in breath is detected based on the magnitude of the infrared light absorption intensity of ethanol.

Figure 3:
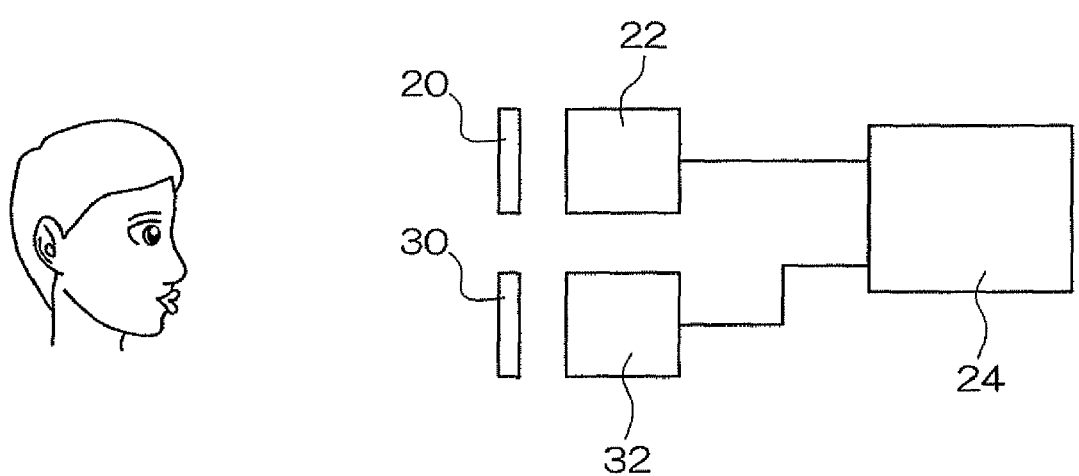
FIG. 3 is a schematic view showing a second exemplary embodiment of the invention.

Next, a second exemplary embodiment of the invention will be explained referring to FIG. 3. The second exemplary embodiment is provided with an infrared light detector for reference for detecting the amount of an infrared light which corresponds to the amount of light To of the light source (face of the driver) in the first exemplary embodiment. Accordingly, in FIG. 3, the portions that correspond to those of FIG. 2 are denoted by the same reference numerals and the explanation thereof is omitted.

The infrared light detector for reference has an optical filter 30 for reference and a photoelectric conversion device 32 for reference. The optical filter 30 for reference allows the transmission of an infrared light having a predetermined wavelength band other than that of an absorption spectrum derived from a C—O stretching vibration of ethanol. The photoelectric conversion device 32 for reference comprises a bolometer, an SOI diode, a thermopile, or the like which converts the infrared light transmitted through the optical filter 30 for reference to an electric signal. An optical filter that may be used as the optical filter 30 comprises a band-cut filter which shuts off an infrared light having a predetermined wavelength band (9 μm to 10 μm) including an absorption spectrum derived from a C—O stretching vibration of ethanol as well as which allows the transmission of an infrared light having a wavelength band other than the predetermined wavelength band.

An ethanol concentration determinator 24 of the exemplary embodiment performs a control for preventing an unauthorized action by calculating the ethanol concentration [EtOH] in breath according the expression (11) using the intensity of an electric signal output from the photoelectric conversion device 32 for reference as the amount of light To of the light source of the expression (11) and determining an ethanol concentration in the breath by comparing a calculated value with a predetermined threshold value.

According to the exemplary embodiment, the ethanol gas concentration contained in breath may be detected using the infrared light emitted from the face of a driver. According to the exemplary embodiment, since the amount of light detected by the infrared light detector for reference is used as the amount of light To of the light source, even if the amount of the infrared light emitted from the face of the driver is changed by the change of a temperature, the variation of a physical condition, and the like, the ethanol concentration may be detected without being affected by the variation of the light source.

Figure 4:
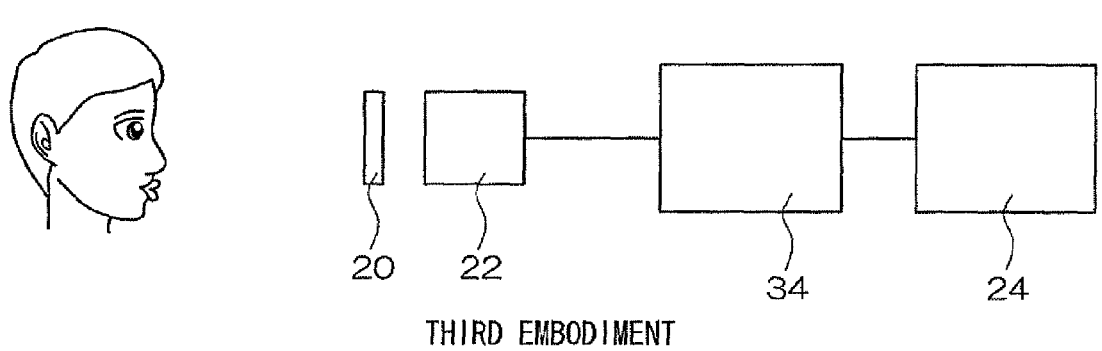
FIG. 4 is a schematic view showing a third exemplary embodiment of the invention.

Next, a third exemplary embodiment of the invention will be explained referring to FIG. 4. The third exemplary embodiment detects an ethanol concentration by extracting only the signal of a breath frequency component corresponding to the timing of breath from the electric signal showing the ethanol gas concentration in the first exemplary embodiment. Accordingly, in FIG. 4, the portions that correspond to those of FIG. 2 are denoted by the same reference numerals and the explanation thereof is omitted.

In the exemplary embodiment, a breath signal filter 34, which comprises a high-pass filter for allowing the transmission of a signal equal to or larger than the breath frequency component from an electric signal output from the photoelectric conversion device 22 for ethanol, is connected between an output side of a photoelectric conversion device 22 and an ethanol concentration determinator 24, and only the electric signal of a component corresponding to the breath frequency component is extracted from the electric signal output from the photoelectric conversion device 22 for ethanol and input to the ethanol concentration determinator 24.

Figure 5:
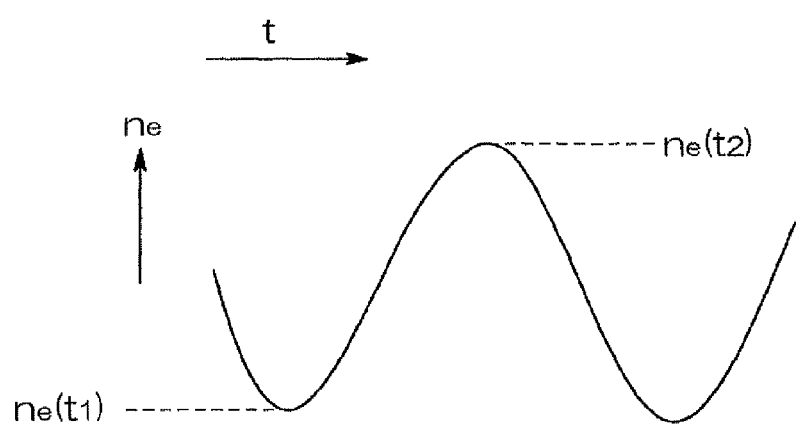
FIG. 5 is a graph showing a time change of an ethanol concentration according to a breath frequency of the third exemplary embodiment.

The ethanol concentration determinator 24 calculates an ethanol concentration, which changes according to a breath frequency as a time passes, according to the expression (11) as shown in FIG. 5 of the exemplary embodiment. The ethanol concentration determinator 24 calculates the amount of change nep=ne($t_2$)−ne($t_1$) (ne($t_2$) shows an ethanol concentration at a time $t_2$, and ne($t_1$) shows an ethanol concentration at a time $t_1$ of a calculated ethanol concentration in a predetermined time ($t_2$-$t_1$) as the ethanol concentration and performs a control for preventing an unauthorized action likewise the above exemplary embodiments. Note that a value from a peak to a peak, i.e., a peak-to-peak value may be used in place of the amount of change nep in the predetermined time ($t_2$-$t_1$), or a rate of change which is an amount of change per unit time or the integration value of the ethanol concentration in a predetermined time may be used.

According to the exemplary embodiment, since an ethanol component in breath is detected and the ethanol concentration is determined as the amount of change nep in a predetermined time, the ethanol concentration may be more accurately detected.

Figure 6:
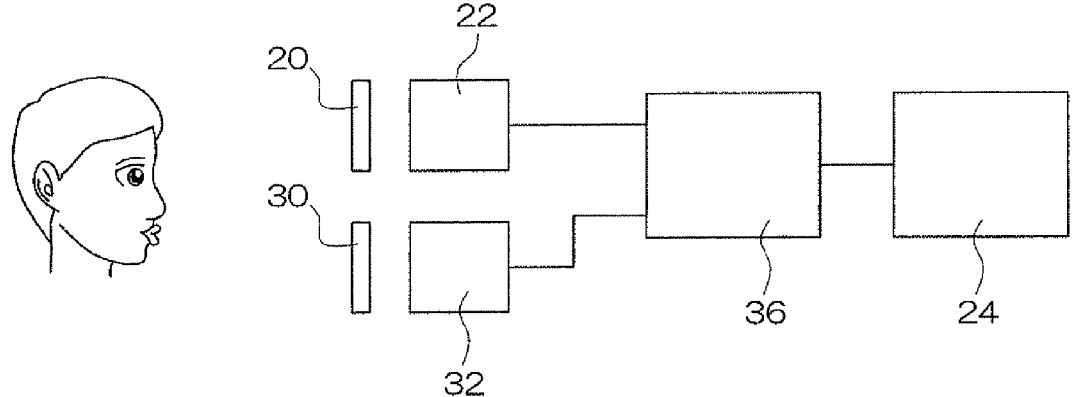
FIG. 6 is a schematic view showing a fourth exemplary embodiment of the invention.

Next, a fourth exemplary embodiment of the invention will be explained referring to FIG. 6. The fourth exemplary embodiment measures an ethanol concentration by extracting only the signals of a breath frequency component corresponding to the timing of breath from the outputs of the photoelectric conversion device for ethanol and the photoelectric conversion device for reference in the second exemplary embodiment. Accordingly, in FIG. 6, the portions that correspond to those of FIG. 3 are denoted by the same reference numerals and the explanation thereof is omitted.

In the exemplary embodiment, a breath signal filter 36 comprising a high-pass filter, which allows the transmission of only the signals of a breath frequency component from electric signals output from a photoelectric conversion device 22 for ethanol and the photoelectric conversion device 32 for reference, is connected between output sides of the photoelectric conversion device 22 for ethanol, the photoelectric conversion device 32 for reference, and an ethanol concentration determinator 24.

Only the electric signals of the component corresponding to the breath frequency component in the electric signals output from the photoelectric conversion devices 22, 32 are extracted by the breath signal filter 36 and input to the ethanol concentration determinator 24.

Figure 7:
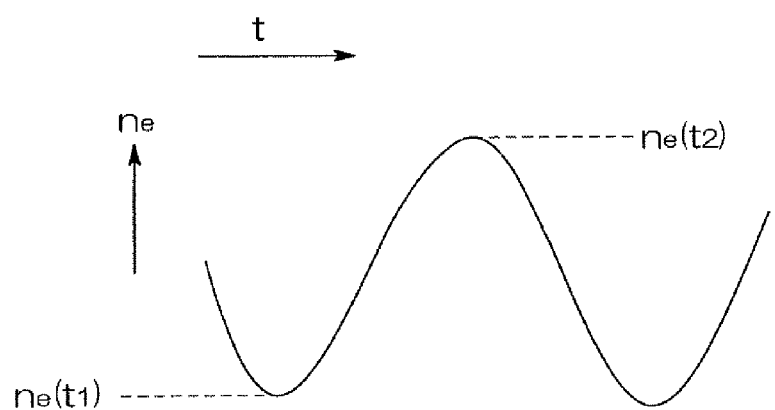
FIG. 7 is a graph showing a time change of an ethanol concentration according to a breath frequency of the fourth exemplary embodiment.

The ethanol concentration determinator 24 of the exemplary embodiment calculates an ethanol concentration, which changes according to a breath frequency as a time changes, as shown in FIG. 7 according to the expression (11) using only the electric signals of the component corresponding to the breath frequency component from electric signals output from the breath signal filter 36 through the photoelectric conversion devices 22, 32. The ethanol concentration determinator 24 calculates the amount of change nep=ne($t_2$)−ne($t_1$) of a calculated ethanol concentration as the ethanol concentration and performs a control for preventing an unauthorized action likewise the above exemplary embodiment.

According to the exemplary embodiment, since the amount of light output from the photoelectric conversion device for reference is used as the amount of light To of the light source, even if the amount of the infrared light emitted from the face of a driver is changed by the change of a temperature, the variation of a physical condition, and the like, the adverse affect to the detection of ethanol concentration caused by the change of the amount of light of a light source may be prevented. Further, since an ethanol component in gas exhausted as breath is detected and the ethanol concentration is determined by the amount of change of the ethanol component, the ethanol concentration may be accurately measured.

Note that the fourth exemplary embodiment explains a case in which the frequency component, which corresponds to the breath frequency component in breath is extracted from the outputs of the photoelectric conversion device for ethanol and the photoelectric conversion device for reference. However, since it is considered that the amount of infrared light emitted from the face of the driver is less varied according to the breath frequency, the breath signal filter may be connected only to the output side of the photoelectric conversion device for ethanol without connecting it to the output side of the photoelectric conversion device for reference.

Next, a fifth exemplary embodiment of the invention will be explained. The fifth exemplary embodiment prevents the adverse affect due to the variation of a distance (light path length) from the face of a driver to an ethanol concentration detector by calculating the ratio of an ethanol concentration to a carbon dioxide gas concentration. Note that, in FIG. 8, the portions that correspond to those of FIG. 2 are denoted by the same reference numerals and the explanation thereof is omitted.

Figure 8:
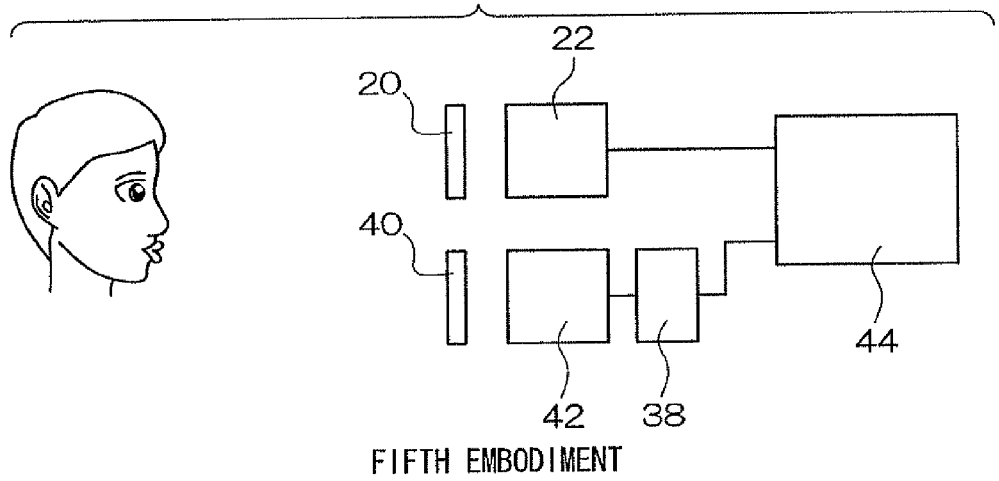
FIG. 8 is a schematic view showing a fifth exemplary embodiment of the invention.

As shown in FIG. 8, the ethanol concentration detector of the exemplary embodiment is provided with the optical filter 20 for ethanol and the photoelectric conversion device 22 for ethanol explained above as well as with an optical filter 40 for carbon dioxide and a photoelectric conversion device 42 for carbon dioxide. The optical filter 40 for carbon dioxide allows the transmission of an infrared light having a predetermined wavelength band (for example, a predetermined wavelength band of 14 μm to 16 μm with a central wavelength of 15 μm) including an absorption spectrum (having a central wavelength of 15 μm as may be understood from FIG. 18) derived from a C—O stretching vibration of carbon dioxide. The photoelectric conversion device 42 for carbon dioxide comprises a bolometer, an SOT diode, a thermopile, or the like for converting an infrared light transmitted through the optical filter 40 to an electric signal.

An breath signal filter 38 comprising a high-pass filter is interposed between the photoelectric conversion device 42 for carbon dioxide and the ethanol concentration determinator 44. The breath signal filter 38 allows the transmission of a signal of a breath frequency component or more from the electric signal output from the photoelectric conversion device 42 for carbon dioxide and attenuates a signal less than the breath frequency component.

The photoelectric conversion device 22 for ethanol and the breath signal filter 38 are connected to an ethanol concentration determinator 44. The ethanol concentration determinator 44 calculates the ratio of the ethanol concentration ne, which is obtained from an electric signal output from the photoelectric conversion device 22 for ethanol, to the carbon dioxide gas concentration nc obtained from the electric signal transmitted through the breath signal filter 38 as the ethanol concentration [EtOH] in breath according to an expression (3) shown below.

$$[EtOH]=ne/nc \qquad (12)$$

where, ne shows the ethanol gas concentration determined by the expression (11), and nc shows the carbon dioxide gas concentration determined by an expression (13) shown below.

$$nc=-\ln(Tc/To)/kc \cdot L \qquad (13)$$

where, Tc shows the amount of transmitted light obtained from an electric signal output from the photoelectric conversion device for carbon dioxide and transmitted through the breath signal filter, and kc shows the absorption coefficient of carbon dioxide. The amount of light To of a light source uses the value explained in the first exemplary embodiment.

Note that the ethanol gas concentration may be determined by the amount of the change of the ethanol concentration (nep=ne($t_2$)−ne($t_1$)) to the amount of change ncp=nc($t_2$)−nc($t_1$) of the carbon dioxide concentration of an expression (20) which is explained below in place of the expression (12). Otherwise, the ethanol gas concentration may be determined by the magnitude of the rate of change one of the ethanol concentration to the rate of change Δnc of the carbon dioxide concentration or may be determined by the magnitude of the ratio of the integration value of the ethanol concentration in a predetermined time to the integration value of the carbon dioxide concentration in the predetermined time.

The reason why the carbon dioxide concentration is used in the exemplary embodiment will be explained below. As described in JP-A No. 2004-279228, when a collection bag is used, there are obtained measured values by multiplying the ethanol gas concentration and the carbon dioxide concentration by the same magnification (x as gas concentrations in the collection bag. Accordingly, when the respective measured values of the ethanol gas concentration and the carbon dioxide concentration are shown by nem, ncm and the carbon dioxide concentration ncb in breath is known, an ethanol concentration neb in breath may be obtained by an expression (14) shown below.

$$(nem/ncm)ncb=(\alpha \cdot neb/\alpha \cdot ncb)ncb=neb \qquad (14)$$

Figure 9:
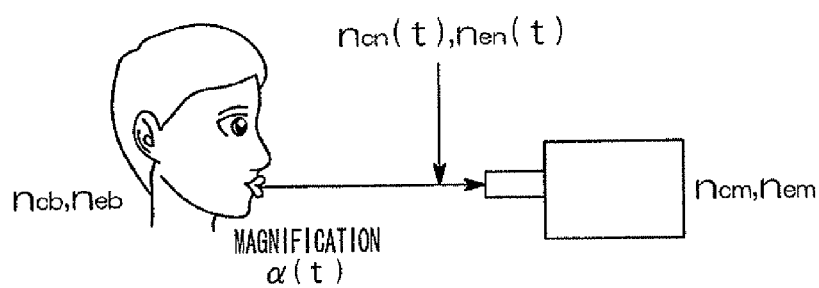
FIG. 9 is a view showing a concept when an ethanol concentration is detected using a carbon dioxide concentration.

On the other hand, a case, in which gas is momentarily collected at a position away from a driver as in the fifth exemplary embodiment, will be explained referring to FIG. 9. In this case, a magnification α(t) changes according to breath rhythm, i.e., a time t. Further, when the collected gas contains ethanol (concentration nen(t)) and carbon dioxide (concentration ncn(t)) in the atmosphere the concentration of each of which changes according to the time t, the ethanol and the carbon dioxide in the atmosphere are detected as noise. Since the measured values nem(t), ncm(t) of ethanol and carbon dioxide are shown by an expression (15) shown below, the ethanol concentration may be detected using a principle of the expression (14).

$$ncm(t)=\alpha(t)ncb+ncn(t)$$

$$nem(t)=\alpha(t)neb+nen(t) \qquad (15)$$

A principle of detection of the exemplary embodiment which uses the carbon dioxide concentration will be explained below. In general, it is assumed that the change of the carbon dioxide concentration in the atmosphere is sufficiently slow as compared with breath rhythm. Accordingly, when ncm(t) is transmitted through the breath signal filter, which comprises the high-pass filter and explained above making use of the difference between the variation frequency of the concentration ncn(t) of the carbon dioxide in the atmosphere and the variation frequency of the concentration of the ethanol in the atmosphere, there may be obtained a breath-signal-filter-transmitted signal ncm'(t)=α(t)ncb from which a signal, which shows the concentration ncn(t) of the carbon dioxide in the atmosphere whose variation frequency is low, is eliminated.

When it is assumed that there is no correlation between α(t) and nen(t), the ethanol concentration neb in breath may be obtained from an expression (16) shown below.

$$\frac{ncm'(t) \cdot nem(t)}{ncm'(t) \cdot ncm(t)} ncb = \frac{neb \cdot ncb \cdot \alpha(t) \cdot \alpha(t)}{ncb \cdot ncb \cdot \alpha(t) \cdot \alpha(t)} ncb \qquad (16)$$

$$= \frac{neb}{ncb} ncb$$

$$= neb$$

Operators O in the expression (16) show a correlation function defined by an expression (17) shown below.

$$x(t) \cdot y(t) = \frac{1}{T} \int_0^T x(s) y(s+t) \, ds \qquad (17)$$

In the expression (17), T shows an arbitrary time length.

When it is assumed as a special case of the above-mentioned that the ethanol and the carbon dioxide in the atmosphere do not vary even a time passes, only concentrations that vary depending on time may be derived as described below by determining nem'(t) and ncm'(t) by transmitting both nem(t) and ncm(t) through the breath signal filter using the breath signal filter. Note that an exemplary embodiment of the special case will be explained below as a sixth exemplary embodiment.

$$nem'(t) = \alpha(t) neb$$

$$ncm'(t) = \alpha(t) ncb \qquad (18)$$

In this case, the ethanol concentration neb in breath may be obtained by a more simple expression (19) shown below.

$$\frac{nem'(t)}{ncm'(t)} ncb = \frac{neb \cdot \alpha(t)}{ncb \cdot \alpha(t)} ncb \qquad (19)$$

$$= \frac{neb}{ncb} ncb$$

$$= neb$$

Figure 10:
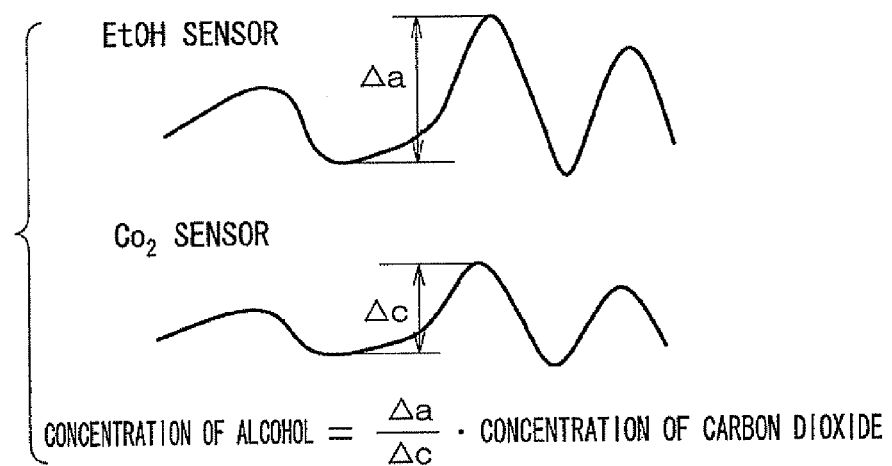
FIG. 10 shows graphs showing changes of a carbon dioxide concentration and an ethanol concentration.

A schematic view resulting from the expression (19) is shown in FIG. 10. As may be understood from the view, the ethanol concentration may be detected by an expression (20) shown below.

Ethanol concentration=(Δa/Δc)·carbon dioxide concentration in breath (20)

where, Δa shows the amount of change (nep=ne($t_2$)−ne($t_1$)), the rate of change, or the integration value in a predetermined time of the ethanol concentration explained above, and Ac shows the amount of change, the rate of change, or the integration value in a predetermined time of the carbon dioxide concentration calculated by the expression (13), and the carbon dioxide concentration in breath is about 3.8% that remains unchanged.

When a light path length, which is shown by the distance from a light source to a detector changes, since the interacting length between gas and an infrared light is changed, there is a possibility that the detected value of the ethanol concentration in breath changes according to the light path length. When breath is diluted by gas such as air and the like, there is a possibility that the ethanol concentration is detected lower than an actual concentration.

Incidentally since the ratio of the carbon dioxide gas concentration in breath remains approximately unchanged, when the ethanol concentration does not change, the ratio of the ethanol concentration to the carbon dioxide concentration in breath remains unchanged even if the light path length is changed or breath is diluted. Thus, in the exemplary embodiment, the ethanol concentration may be accurately detected even if the light path length is changed or breath is diluted by calculating the ratio of the ethanol concentration to the detected carbon dioxide concentration in breath.

Figure 11:
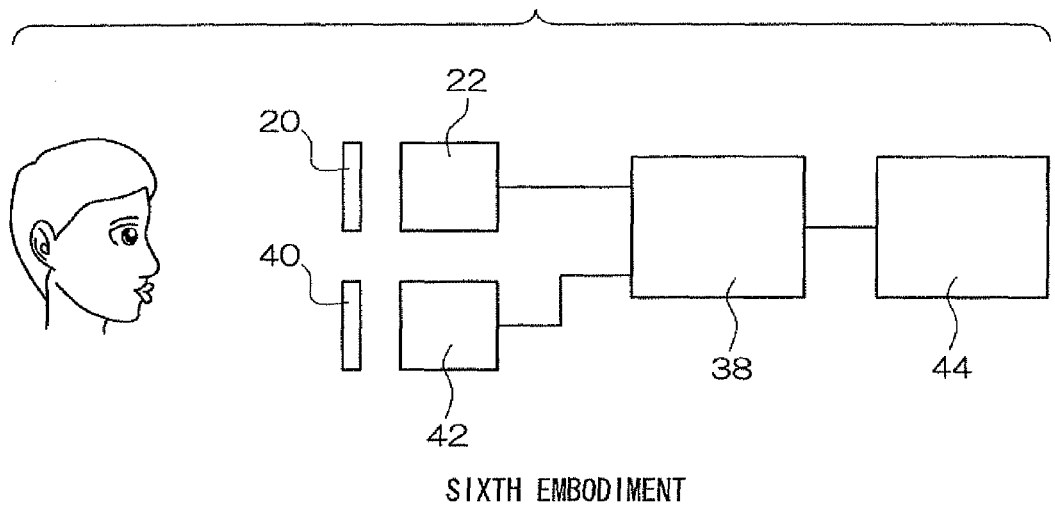
FIG. 11 is a schematic view showing a sixth exemplary embodiment of the invention.

Next, the sixth exemplary embodiment of the invention will be explained referring to FIG. 11. The sixth exemplary embodiment is an exemplary embodiment of a case in which it is assumed that the concentrations of the ethanol and the carbon dioxide in the atmosphere change more slowly than the change of breath which is explained in the detection principle using the carbon dioxide concentration of the above exemplary embodiment. In the exemplary embodiment, only the signal of a component corresponding to timing of breath is extracted from the output of the photoelectric conversion device for ethanol and the output of the photoelectric conversion device for carbon dioxide in the fifth exemplary embodiment, and the ratio of the ethanol concentration to the carbon dioxide concentration in breath is detected as the ethanol concentration. Accordingly, in FIG. 11, the portions that correspond to those of FIG. 8 are denoted by the same reference numerals and the explanation thereof is omitted.

In the exemplary embodiment, a breath signal filter 38 comprising a high-pass filter, which allows the transmission of the signals of a breath frequency component or more from electric signals output from photoelectric conversion devices 22, 42, is connected between output sides of the photoelectric conversion device 22 for ethanol, the photoelectric conversion device 42 for carbon dioxide and an ethanol concentration determinator 44. The electric signals of the component corresponding to the breath frequency component in the electric signals output from the photoelectric conversion devices 22, 42 are extracted by the breath signal filter 38 and input to the ethanol concentration determinator 44.

Figure 12:
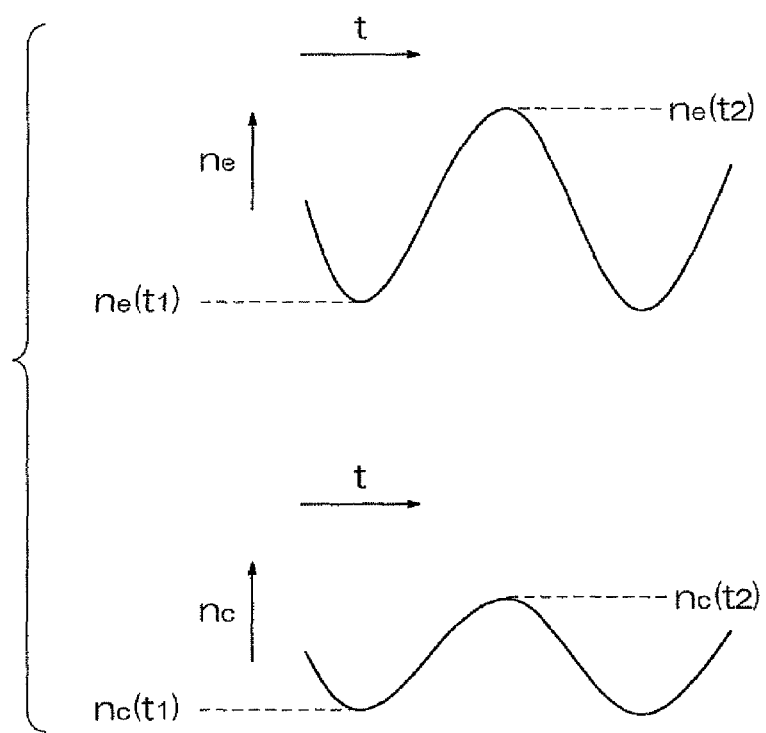
FIG. 12 shows graphs showing time changes of an ethanol concentration and carbon dioxide concentration of the sixth exemplary embodiment.

The ethanol concentration determinator 44 of the exemplary embodiment calculates an ethanol concentration, which changes according to the breath frequency as a time changes, according to the expression (12) using the electric signals of the component corresponding to the breath frequency component from electric signals output from the breath signal filter 38 through the photoelectric conversion devices 22, 42. The ethanol concentration determinator 44 calculates the ratio of the amount of change ((ne($t_2$)−ne($t_1$)) of the ethanol concentration to the amount of change (nc($t_2$)−nc($t_1$)) of the carbon dioxide concentration according to the following expression (21) and performs a control for preventing an unauthorized action likewise the above respective exemplary embodiments. Note that a rate of change or an integration value in a predetermined time may be used in place of the amount of change as explained above.

$$[EtOH]=(ne(t_2)-ne(t_1))/(nc(t_2)-nc(t_1)) \quad (21)$$

where, as shown in FIG. 12, $ne(t_2)$, $ne(t_1)$ show the ethanol gas concentrations at times $t_2$, $t_1$ shown by ne in the following expression, and $nc(t_2)$, $nc(t_1)$ show the carbon dioxide concentrations at the times $t_2$, $t_1$ shown by nc of the following expression.

$$ne=-\ln(Te/To)/ke\cdot L$$

$$nc=-\ln(Tc/To)/kc\cdot L \quad (22)$$

According to the exemplary embodiment, since the ratio of the ethanol concentration to the carbon dioxide concentration in breath is detected as the ethanol concentration by extracting the breath frequency component, the ethanol concentration may be accurately detected as to a case in which it is assumed that the ethanol and the carbon dioxide in breath changes more slowly than the change of breath.

Figure 13:
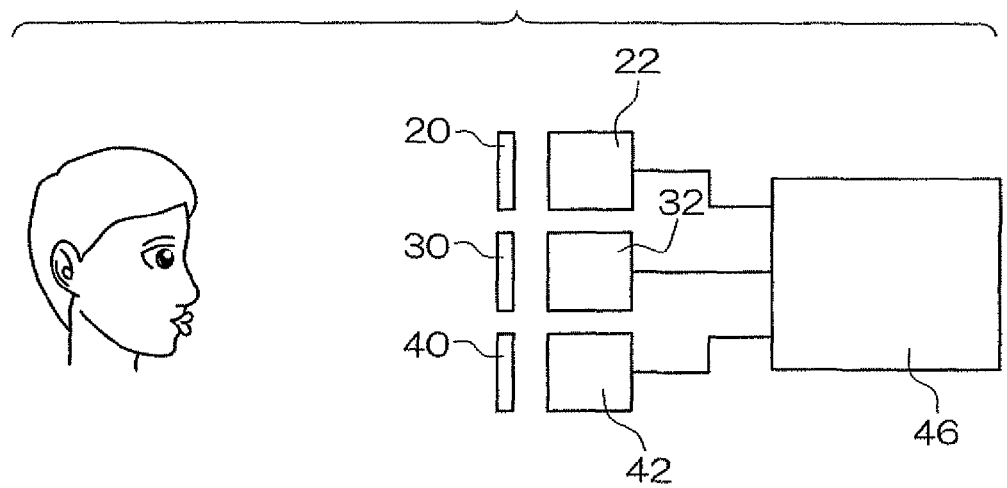
FIG. 13 is a schematic view showing a seventh exemplary embodiment of the invention.

Next, a seventh exemplary embodiment of the invention will be explained referring to FIG. 13. The seventh exemplary embodiment is arranged such that the optical filter for reference and the photoelectric conversion device for reference explained in the second exemplary embodiment are disposed to a mode in which the breath signal filter of the fifth exemplary embodiment is not disposed and the amount $T_0$ of infrared light emitted from the face of the driver as a light source is detected. Accordingly, in FIG. 13, the portions that correspond to those of FIGS. 3 and 8 are denoted by the same reference numerals and the explanation thereof is omitted.

A photoelectric conversion device 22 for ethanol, a photoelectric conversion device 32 for reference, and a photoelectric conversion device 42 for carbon dioxide of the exemplary embodiment are connected to an ethanol concentration determinator 46, respectively. The ethanol concentration determinator 46 calculates the ratio of an ethanol concentration ne to a carbon dioxide gas concentration nc as the ethanol concentration [EtOH] in breath according to the expression (12). In this case, as explained in the second exemplary embodiment, the amount of transmitted light, which is obtained from an electric signal output from the photoelectric conversion device 32 as the amount of light $T_0$ of the light source, is used as the ethanol concentration ne.

According to the exemplary embodiment, an error due to the variation of the amount of light of the light source may be prevented by using the optical filter for reference and the photoelectric conversion device for reference as well as the ethanol concentration may be accurately detected even if a light path length is changed or breath is diluted by calculating the ratio of the ethanol concentration to the carbon dioxide concentration in breath as explained in the second exemplary embodiment.

Note that the seventh exemplary embodiment may be provided with a breath signal filter 38 comprising a high-pass filter and interposed between the photoelectric conversion device 42 for carbon dioxide and the ethanol concentration determinator 44 so that the ethanol concentration is detected according to the expression (1) or (2) likewise the fifth exemplary embodiment, wherein the breath signal filter 38 allows a signal of a breath frequency component or more from the electric signal output from the photoelectric conversion device 42 for carbon dioxide to transmit therethrough and attenuates a signal less than the breath frequency component.

Figure 14:
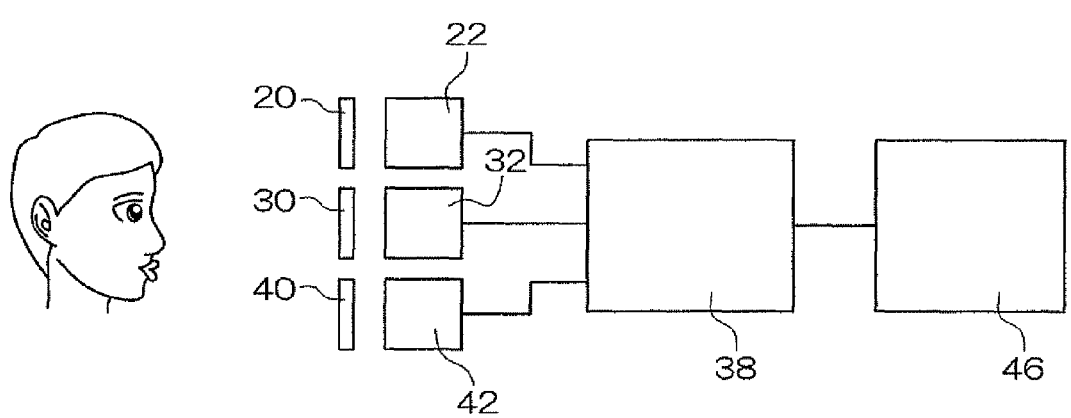
FIG. 14 is a schematic view showing an eighth exemplary embodiment of the invention.

Next, an eighth exemplary embodiment of the invention will be explained referring to FIG. 14. The exemplary embodiment extracts only the signals of a component corresponding to timing of breath from the output of the photoelectric conversion device for ethanol, the output of the photoelectric conversion device for reference and the output of the photoelectric conversion device for carbon dioxide in the seventh exemplary embodiment and detects the ratio of an ethanol concentration to the carbon dioxide concentration in breath as an ethanol concentration. Accordingly, in FIG. 14, the portions that correspond to those of FIG. 13 are denoted by the same reference numerals and the explanation thereof is omitted.

In the exemplary embodiment, a breath signal filter 38 comprising a high-pass filter is connected between the output sides of a photoelectric conversion device 22 for ethanol, a photoelectric conversion device 32 for reference, and a photoelectric conversion device 42 for carbon dioxide and an ethanol concentration determinator 46, the breath signal filter 38 allowing the transmission of signals of a breath frequency component or more from electric signals output from the photoelectric conversion devices 22, 32, and 42. Only the electric signals of the component corresponding to the breath frequency component or more in the electric signals output from the photoelectric conversion devices 22, 32, and 42 are extracted by the breath signal filter 38 and input to the ethanol concentration determinator 46.

Figure 15:
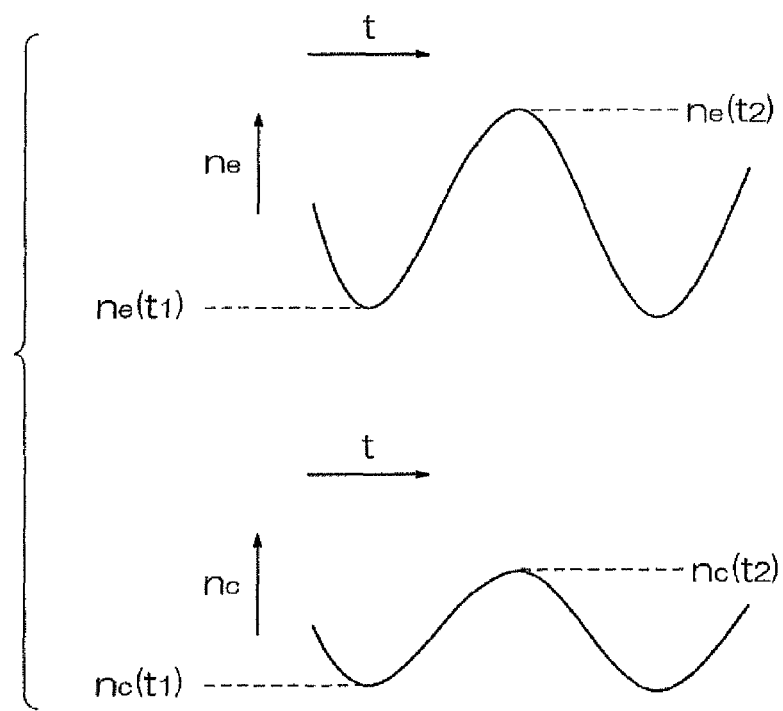
FIG. 15 shows graphs showing time changes of an ethanol concentration and carbon dioxide concentration of the eighth exemplary embodiment.

In the ethanol concentration determinator 46 of the exemplary embodiment, the ratio of the amount of change ($=ne(t_2)-ne(t_1)$) of an ethanol gas concentration to the amount of change ($=nc(t_2)-nc(t_1)$) of a carbon dioxide gas concentration shown in FIG. 15 is calculated as an ethanol concentration according to an expression (23) shown below using the electric signals of the component corresponding to the breath frequency component in the electric signals output from the breath signal filter 38 through the photoelectric conversion devices 22, 32, and 42, and a control for preventing an unauthorized action is performed likewise the above respective exemplary embodiments. Note that a rate of change or an integration value in a predetermined time may be used in place of the amount of change as explained above.

$$[EtOH]=\{ne(t_2)-ne(t_1)\}/\{nc(t_2)-nc(t_1)\} \quad (23)$$

According to the exemplary embodiment, an error due to the variation of the amount of light of a light source may be prevented as well as since the ratio of the ethanol concentration to the carbon dioxide concentration in breath is detected as the ethanol concentration by extracting the breath frequency component, the ethanol concentration may be more accurately measured.

Note that, in the eighth exemplary embodiment, although the example, in which the electric signals output from the photoelectric conversion devices 22, 32, and 42, are transmitted through the breath signal filter 38, is explained. However, the breath signal filter 38 may be interposed between the photoelectric conversion device 42 for carbon dioxide and an ethanol concentration determinator 44 likewise the fifth exemplary embodiment, and an ethanol concentration may be detected using a signal transmitted through the breath signal filter 38 and an electric signal output from the photoelectric conversion device 22.

The above exemplary embodiment explains a case in which the fifth to eighth exemplary embodiments detect an accurate ethanol concentration by detecting the carbon dioxide concentration in breath and calculating the ratio of an ethanol concentration to the carbon dioxide concentration in breath to accurately detect the ethanol concentration even if a light path length is changed or breath is diluted.

In contrast the ratio of the vapor concentration in breath remains approximately unchanged likewise the ratio of a carbon dioxide gas concentration. Accordingly, the vapor concentration may be used in place of the carbon dioxide gas concentration in the fifth to eighth exemplary embodiments explained above.

A case, in which the vapor concentration is used in place of the carbon dioxide gas concentration in the eighth exemplary embodiment, will be explained below referring to FIG. 16 as an example for using the vapor concentration in place of the carbon dioxide gas concentration. Note that, in FIG. 16, the portions that correspond to those of FIG. 14 are denoted by the same reference numerals and the explanation thereof is omitted.

Figure 16:
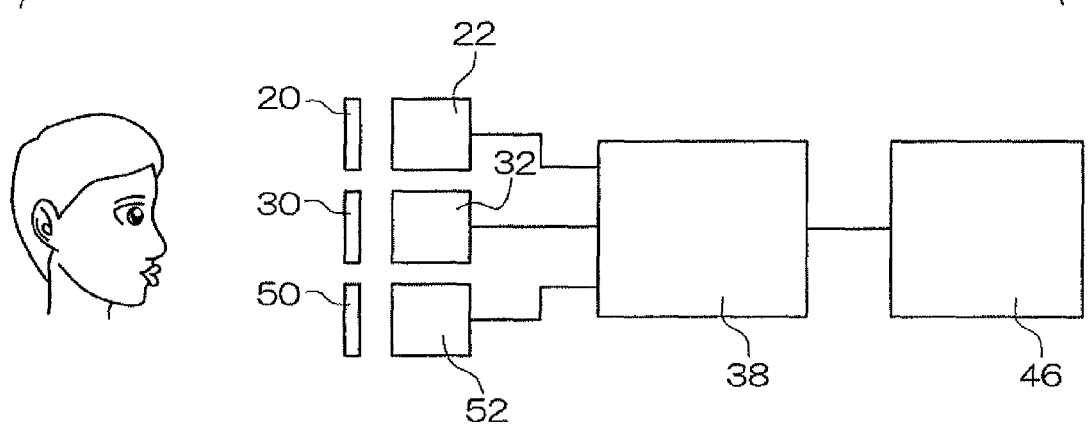
FIG. 16 is a schematic view showing a ninth exemplary embodiment of the invention.

As shown in FIG. 16, in the exemplary embodiment, an optical filter 50 for vapor, which allows the transmission of an infrared light having a predetermined wavelength band with an absorption spectrum of vapor as its central wavelength, is disposed in place of the optical filter 40 for carbon dioxide as well as a photoelectric conversion device 52 for vapor, which converts infrared light transmitted through the optical filter 50 for vapor to an electric signal is disposed in place of the photoelectric conversion device 42 for carbon dioxide.

An breath signal filter 38 comprising a band-pass filter is connected between the output sides of a photoelectric conversion device 22 for ethanol, a photoelectric conversion device 32 for reference, and a photoelectric conversion device 52 for vapor and an ethanol concentration determinator 46, the breath signal filter 38 allowing the transmission of signals of a breath frequency component from electric signals output from the photoelectric conversion devices 22, 32, and 52. Only the electric signals of the component corresponding to the breath frequency component in the electric signals output from the photoelectric conversion devices 22, 32, and 52 are extracted by the breath signal filter 38 and input to the ethanol concentration determinator 46.

Figure 17:
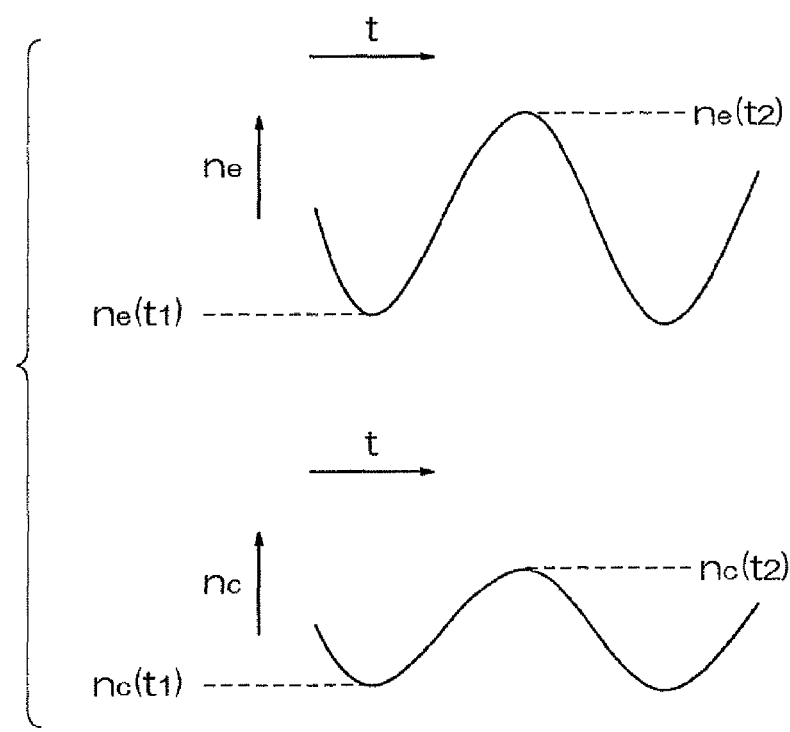
FIG. 17 shows graphs showing time changes of an ethanol concentration and a vapor concentration of the ninth exemplary embodiment.

In the ethanol concentration determinator 46 of the exemplary embodiment, the ratio of the amount of change ($=ne(t_2)-ne(t_1)$) of an ethanol gas concentration to the amount of change ($=nw(t_2)-nw(t_1)$) of a vapor concentration shown in FIG. 17 is calculated as an ethanol concentration according to an expression (24) shown below using the electric signals of the component corresponding to the breath frequency component in the electric signals output from the breath signal filter 38 through the photoelectric conversion devices 22, 32, and 52, and a control for preventing an unauthorized action is performed likewise the above respective exemplary embodiments. Note that a rate of change or an integration value in a predetermined time may be used in place of the amount of change as explained above.

$$[EtOH]=\{ne(t_2)-ne(t_1)\}/\{nw(t_2)-nw(t_1)\} \quad (24)$$

Note that when the vapor concentration is detected in place of the detection of the concentration of the carbon dioxide, the breath signal filter 38 may be interposed between the photoelectric conversion device 42 for carbon dioxide and an ethanol concentration determinator 44 likewise the fifth exemplary embodiment as explained in the detection of the concentration of the carbon dioxide, and an ethanol concentration may be detected using the signal transmitted through the breath signal filter 38 and the electric signal output from the photoelectric conversion device 22.

Next, a result of measurement of ethanol measured by a far infrared light detector using a breath model containing ethanol and the face of a person as a light source will be explained.

Figure 23:
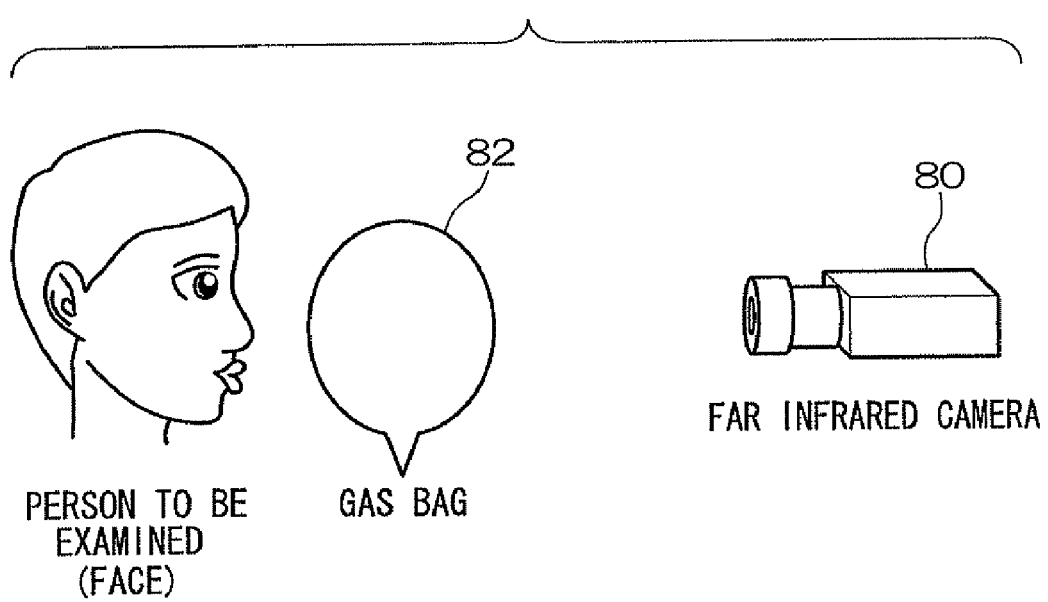
FIG. 23 is a schematic view showing a state that ethanol is measured by a far infrared camera using the face of a person as a light source.

As shown in FIG. 23, a result of measurement of a case, which is performed by using a far infrared camera 80 as the far infrared light detector, disposing a gas bag 82 filled with ethanol gas as the breath model containing ethanol between the face of the person and the far infrared camera 80, and picking up the face of the person through the gas bag 82, will be explained here.

Figure 25:
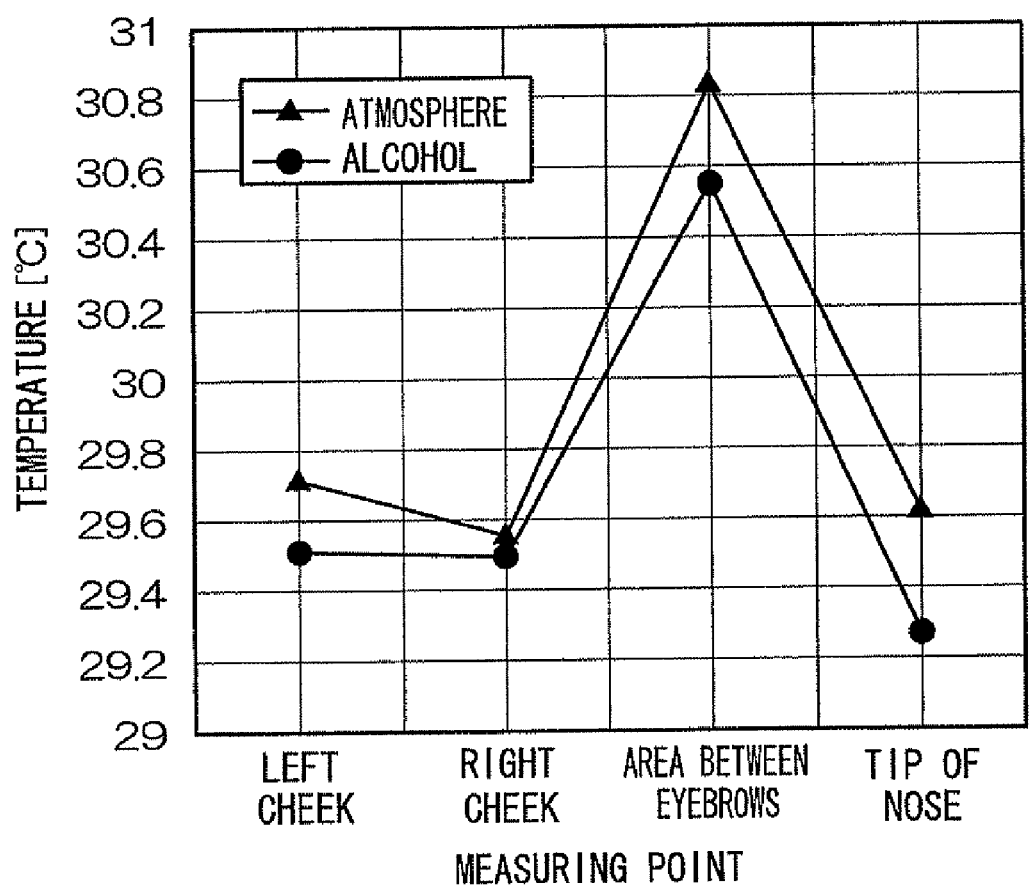
FIG. 25 is a graph showing the temperatures of a face picked up by the far infrared camera in comparison with each other.

FIG. 24 shows an image of a gas bag filled with atmospheric air and picked up by the far infrared camera ((1) of FIG. 24) and an image of a gas bag filled with ethanol gas of 2 mg/l and picked up by the far infrared camera ((2) of FIG. 24) in comparison with each other. Further, FIG. 25 shows a result of comparison of the temperatures of the picked-up face image in the four portions thereof, i.e., the right and left cheeks, the area between eyebrows, and the tip of the nose. When this is explained as to the tip of the nose (light path length in the gas bag: 150 mm), a drop of temperature of about 0.34° C. is observed. A reason why the phenomenon occurs resides in that far infrared light emitted from the face is absorbed to the ethanol gas and measured as a face temperature as a result. Since the minimum difference of temperature that may be detected by the far infrared camera is 0.01° C., ethanol gas of an amount of 0.06 mg/l or more contained in breath may be detected in the above measurement.

It may be understood from the result of measurement that the concentration of ethanol may be accurately measured by the far infrared light detector also when the face of a person is used as a light source.

The invention, which pays attention to that the change of concentration of carbon dioxide (or vapor) in the atmosphere is sufficiently slower the breath rhythm, has been explained as to the exemplary embodiment using the infrared light detector for detecting an infrared light absorption intensity. In the invention, which pays attention to that the change of concentration of carbon dioxide (or vapor) in the atmosphere is sufficiently slower the breath rhythm, an ethanol gas sensor for detecting the concentration of ethanol gas using an oxide semiconductor, a carbon dioxide sensor for detecting the concentration of carbon dioxide using a solid electrolyte, or a vapor sensor for detecting the concentration of vapor using an oxide semiconductor or a polymer film capacitance may be used in place of the infrared light detector. Further, since the ratio of concentration of oxygen in breath remains approximately unchanged likewise the ratio of concentration of carbon dioxide gas, an oxygen sensor for detecting the concentration of oxygen using a solid electrolyte may be used in place of the vapor sensor and the carbon dioxide sensor.

More specifically, when a sensor for detecting gas is used, the concentration of ethanol may be detected using a correction sensor comprising an oxide semiconductor sensor for detecting the concentration of ethanol and a gas sensor for detecting the concentration of correction gas comprising at least one kind of gas of vapor, carbon dioxide, and oxygen.

Figure 19:
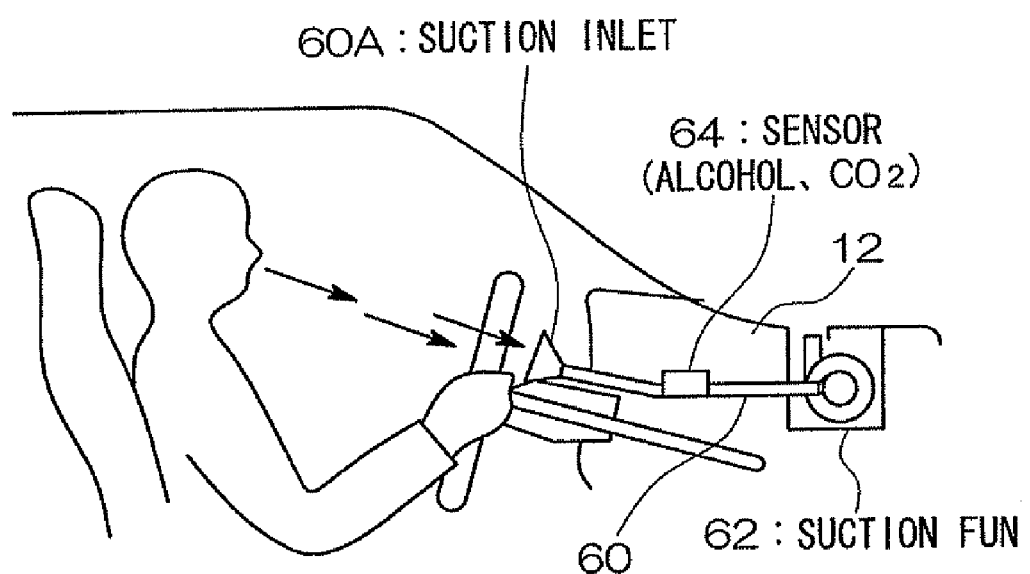
FIG. 19 is a schematic view showing a tenth exemplary embodiment of the invention.

Next, a tenth exemplary embodiment making use of a gas sensor will be explained below referring to FIG. 19. The exemplary embodiment detects the concentrations of ethanol and carbon dioxide making use of the gas sensor. As shown in FIG. 19, there is attached a slender cylindrical gas collection pipe 60 to the extreme end of which a suction inlet 60A whose diameter is enlarged is formed. A suction fun 62 is disposed to the base end portion of the gas collection pipe 60 and is driven to suck breath of a driver from the suction inlet 60A.

A sensor 64, which has an ethanol gas sensor (for example, TGS822 using a tin oxide semiconductor (trade name, manufactured by Figaro Engineering Inc.) as an alcohol sensor for detecting the concentration of ethanol gas using a tin oxide semiconductor and a carbon dioxide sensor (for example, trade name: CDM44160, manufactured by Figaro Engineering Inc.) for detecting the concentration of carbon dioxide using a solid electrolyte, is attached to the inside of an intermediate portion of the gas collection pipe 60. An ethanol concentration determinator (not shown) similar to that explained in the above exemplary embodiments is connected to the sensor.

According to the exemplary embodiment, the breath of the driver is sucked from the suction inlet 60A by driving the suction fun 62, and the concentration of the ethanol gas in the breath is detected by the ethanol gas sensor as well as the concentration of the carbon dioxide in the breath is detected by the carbon dioxide sensor.

The concentrations of the carbon dioxide and the ethanol gas contained in the breath, which are detected by the sensors, are input to the ethanol concentration determinator, the concentration of the ethanol gas is detected based on the magnitude of the concentration of the ethanol to the detected concentration of the carbon dioxide according to the expression (1) or (2), and a control is performed to prevent an unauthorized action as explained above.

Note that, in the exemplary embodiment, the concentrations of ethanol and vapor contained in the breath may be detected using a vapor sensor for detecting the concentration of vapor using an oxide semiconductor in place of the carbon dioxide sensor and the concentration of ethanol gas may be detected based on the magnitude of the concentration of ethanol to the detected concentration of vapor as explained below.

Figure 20:
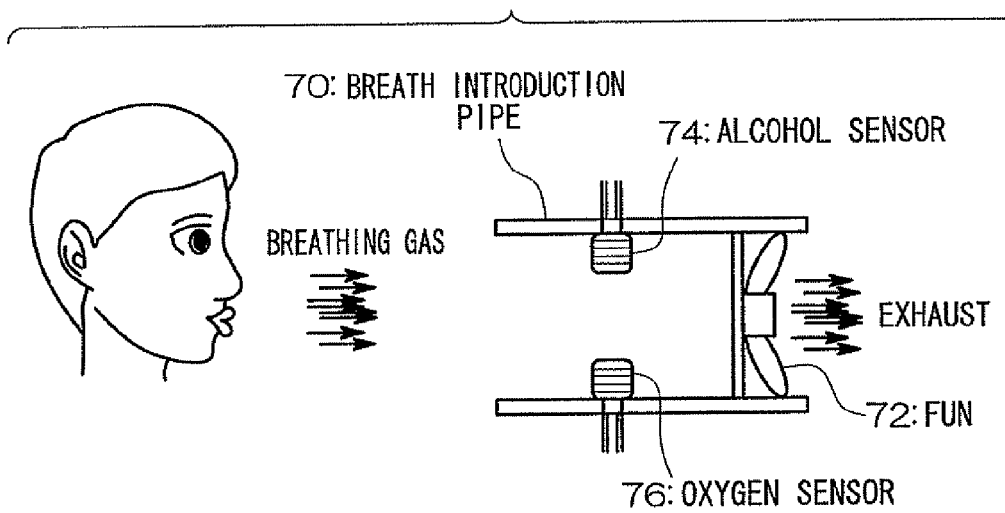
FIG. 20 is a schematic view showing an eleventh exemplary embodiment of the invention.

Next, an eleventh exemplary embodiment, which detects the concentration of ethanol making use of a gas sensor using an oxide semiconductor as well as detects the concentration of oxygen contained in air making use of a gas sensor using a zirconia solid electrolyte, will be explained referring to FIG. 20. As shown in FIG. 20, a suction fun 72 is disposed to one end of a cylindrical breath introduction pipe 70 and is driven to suck breath of a person such as a driver from the other end of the breath introduction pipe 70.

An alcohol sensor 74, which detects the concentration of an ethanol gas component using an oxide semiconductor, and an oxygen sensor 76, which detects the concentration of oxygen using a zirconia solid electrolyte, are disposed to the inside of an intermediate portion of the breath introduction pipe 70 in confrontation with each other. These sensors are connected to an ethanol concentration determinator (not shown) similar to that explained in the above exemplary embodiments.

The alcohol sensor is a sensor for detecting the ethanol component contained in air flowing in the breath introduction pipe, and, for example, TGS822 (trade name, manufactured by Figaro Engineering Inc.) using an oxide tin semiconductor may be used.

The oxygen sensor 76 is a sensor for detecting oxygen flowing in the breath introduction pipe 70, and, for example, FCX-MVL (trade name, manufactured by Fujikura Ltd. using a zirconia solid electrolyte may be used.

According to the exemplary embodiment, when the suction fun 72 is driven, breath from a person is sucked into the breath introduction pipe from the other end of the pipe and exhausted to the back surface of the fan after it comes into contact with the alcohol sensor and the oxygen sensor When the breath comes into contact with the alcohol sensor and the oxygen sensor, the concentration of the ethanol gas component in air containing breath is detected by the alcohol sensor as well as the concentration of the oxygen in the air containing breath is detected by the oxygen sensor. With this operation, the concentrations of the ethanol component and the oxygen in air detected by the sensors similar to those of the above exemplary embodiments are input to an ethanol concentration determinator, the concentration of the ethanol gas is detected based on the magnitude of the concentration of the ethanol component to the detected concentration of the oxygen, and a control is performed to prevent an unauthorized action as explained above. In the exemplary embodiment, the ethanol gas concentration is detected using the amount of change, the rate of change, and the integration value in a predetermined time of the oxygen concentration detected by the expression (1) or (2) and the oxygen sensor as well as using the oxygen concentration in breath (for example, about 15.2% and remains unchanged).

Note that, when the oxygen concentration is used, since the concentration of oxygen in breath is reduced as compared with that in the atmosphere contrary to the case in which the carbon dioxide concentration explained in the above exemplary embodiment is used, the value detected by the oxygen sensor is more reduced than the value in the atmosphere output from the oxygen sensor.

The above exemplary embodiments have explained the cases that the ethanol concentration is detected according to the expression (1) or (2) assuming that the correction gas comprising any one type of gas of ethanol, carbon dioxide, oxygen, and vapor in breath does not vary even a time passes, i.e., the amount of breath exhausted to the atmosphere is sufficiently small (breath is diluted in the atmosphere).

However, the breath exhausted from person is mixed with air, is arbitrarily diluted therewith, and comes into contact with the alcohol sensor and the correction sensor (oxygen sensor, carbon dioxide sensor, or vapor sensor). Since the above expressions assume that the amount of breath is sufficiently small to the amount of the atmosphere when breath is caused to directly come into contact with a sensor through an introduction pipe such as a nozzle (when breath dilution magnification is 1), an error occurs due to a volume of breath.

Accordingly in the exemplary embodiment, a concept of a breath dilution magnification may be introduced in consideration of the affect of the volume of breath to more accurately detect the ethanol concentration. The breath dilution magnification may be calculated as shown in an expression (25) shown below using oxygen concentrations (or carbon dioxide concentrations or vapor concentrations) before and after breath is detected. The expression (25) shows a case in which an oxygen concentration is used as a correction gas concentration.

$$[EtOH]breath=([EtOH]peak-EtOH]base) \times Di+[EtOH]base \quad (25)$$

$$Di=([O_2]breath-[O_2]base)/(O_2]peak-[O_2]base) \quad (26)$$

where, Di is a breath dilution magnification showing the ratio at which breath is diluted with air until it reaches a sensor,

[$O_2$]breath: an oxygen concentration in breath,

[$O_2$]base: the concentration output from an oxygen sensor before breath is introduced,

[$O_2$]peak: the maximum value of the concentration output from the oxygen sensor when breath is introduced,

[EtOH]breath: the ethanol concentration in breath,

[EtOH]base: the concentration output from an alcohol sensor before breath is introduced, and

[EtOH]peak: the maximum value of the concentration output from the alcohol sensor when breath is introduced.

The calculate of the expression (25) is introduced paying attention to that even if breath is arbitrarily diluted, the dilution magnification of ethanol is equal to the dilution magnification of oxygen at all times. Since the oxygen concentration in breath [$O_2$]breath is always unchanged (for example, 15.2%), first, the breath dilution magnification Di is calculated from the concentration value of the output from the oxygen sensor. Next, since ethanol is diluted at the breath dilution magnification Di, the ethanol concentration in breath [EtOH]breath is calculated from the breath dilution magnification Di and the concentration value of the output from the alcohol sensor.

Note that although the maximum values are used above as the values (output concentrations) output from the alcohol sensor and the oxygen sensor when breath is introduced. However, the maximum values need not be necessarily used, and when a value, is output after the breath, which is introduced into the breath introduction pipe comes into contact with the alcohol sensor and the oxygen sensor, the ethanol gas concentration in breath may be calculated using the amount of change or the rate of change of the above output value likewise the above mentioned.

Figure 21:
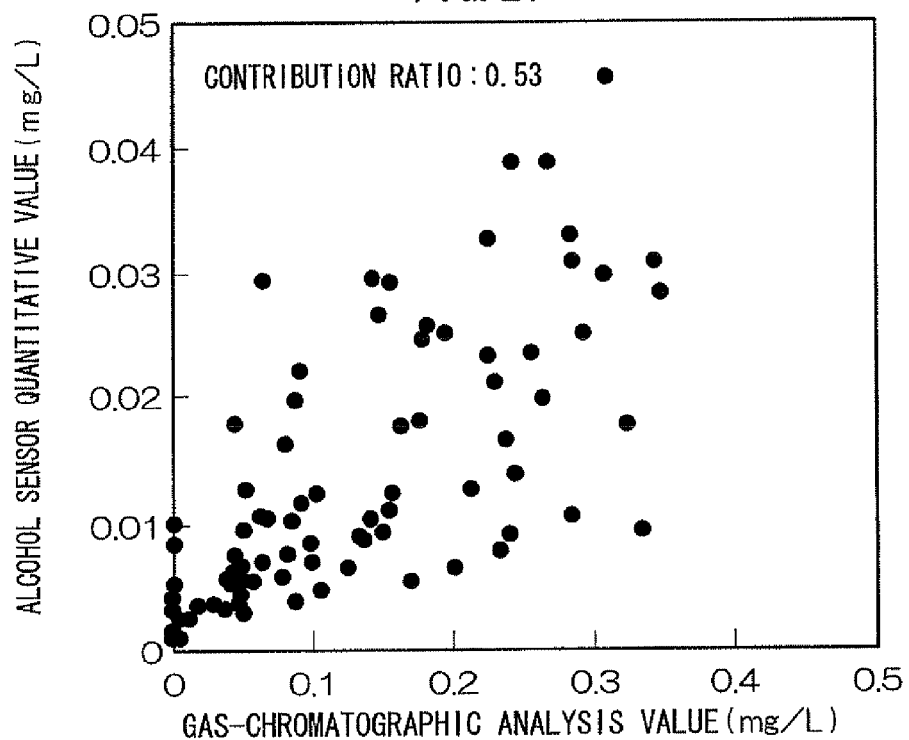
FIG. 21 is a view showing the correlation between the quantitative value of an alcohol sensor and the analysis value of a gas chromatogram of the eleventh exemplary embodiment.
Figure 22:
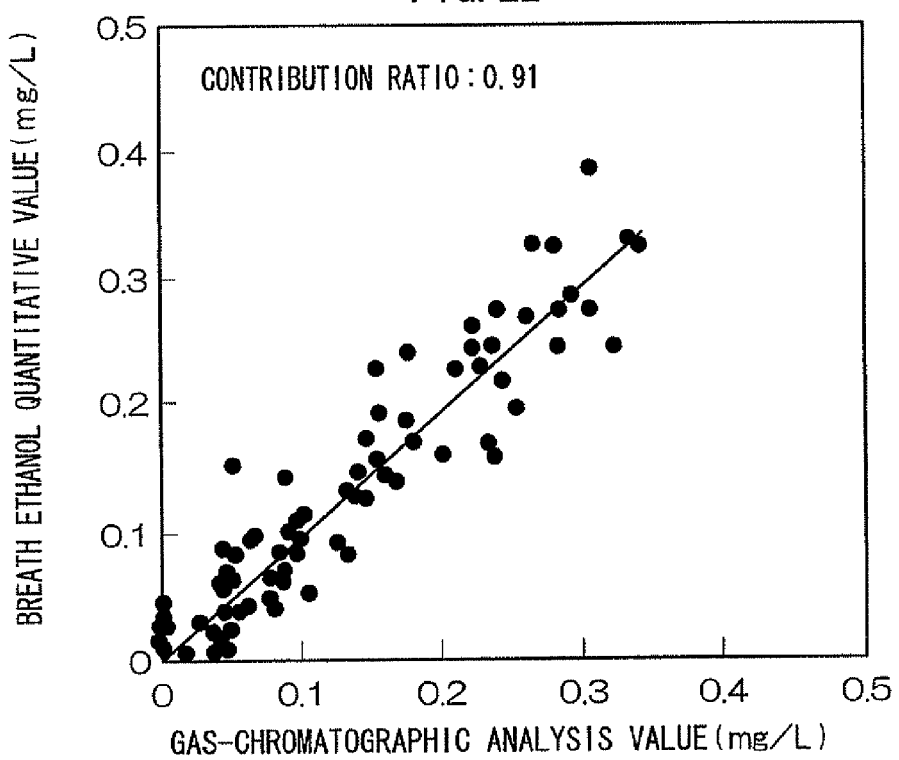
FIG. 22 is a view showing the correlation between the quantitative value of ethanol contained in breath and then analysis value of the gas chromatogram of the eleventh exemplary embodiment.

FIGS. 21 and 22 show a result of check when breaths of 18 persons to be checked, who drank alcohol, were collected, the concentrations of the breaths were analyzed by a gas chromatograph, the values of the analysis were obtained, and the values were compared with the quantitative value of ethanol contained in breath calculated using the expression (25) in the exemplary embodiment. As shown in FIG. 21, since the breaths exhausted from the persons were diluted with the atmosphere at an arbitrary dilution magnification, the ethanol concentrations measured by the alcohol sensor exhibit a low correlation (contribution ratio: 0.53) to the values analyzed by the gas chromatograph.

In contrast, when the ethanol concentration contained in breath was calculated based on the expression (15) using the measured ethanol gas concentration and the breath dilution magnification calculated from the value output from the oxygen sensor, a good correlation of the contribution ratio of 0.91 was found between quantitative value of the ethanol contained in breath and the value analyzed by the gas chromatograph as shown in FIG. 22.

Note that the example using the oxygen sensor as the correction sensor was explained above. However, the ethanol concentration may be calculated by the same method as that explained above by using a carbon dioxide sensor in place of the oxygen sensor and calculating the breath dilution magnification from the change of the concentration of carbon dioxide using the concentration of carbon dioxide in place of the concentration of oxygen of the expression (26). When the carbon dioxide sensor is used, the carbon dioxide concentration in breath is about 3.8% that remains unchanged.

Further, the ethanol concentration may be calculated by the same method as that explained above by using a vapor sensor in place of the oxygen sensor and calculating the breath dilution magnification from the change of the concentration of vapor using the concentration of vapor in place of the concentration of oxygen of the expression (26). When the vapor sensor is used, the value of the concentration of saturated vapor of 34° C., for example, is used as the fixed value of the concentration of vapor contained in breath. Further, a vapor sensor using an oxide tin semiconductor as an oxide semiconductor (for example, TGS2180 (trade name, manufactured by Figaro Engineering Inc.) may be used as the vapor sensor.

As explained above, according to the eleventh exemplary embodiment, the ethanol concentration may be accurately detected also when not only breath is diluted with the atmosphere but also when breath directly comes into contact with the sensor without being diluted.

The expression (25) may be modified and shown as follows.

$$[EtOH]breath \, \Delta a/\Delta_O([O_2]breath-[O_2]base)+[EtOH]base \quad (27)$$

where, as described above, $\Delta a$ shows the amount of change, the rate of change of the concentration of ethanol, and $\Delta_O$ shows the amount of change, the rate of change, or the integration value in a predetermined time of the concentration of oxygen. The amount of change, the rate of change, or the integration value in a predetermined time of the concentration of carbon dioxide or the amount of change, the rate of change, or the integration value in a predetermined time of the concentration of vapor may be used in place of $\Delta_O$.

Accordingly, in the exemplary embodiment, the ethanol concentration may be calculated based on the expression (27) using the amount of change, the rate of change, or the integration value in a predetermined time of the ethanol concentration, the amount of change, the rate of change, or the integration value in a predetermined time of the oxygen concentration (or the carbon dioxide concentration or the vapor concentration), the difference obtained by subtracting the oxygen concentration (or the carbon dioxide concentration or the vapor concentration) in the atmosphere detected by the sensor from the oxygen concentration (or carbon dioxide concentration or the vapor concentration) in breath that is a fixed value, and the ethanol concentration in the atmosphere detected by the sensor without calculating the breath dilution magnification Di.

As explained above, a breath signal filter comprising a high-pass filter and the like, which allows the transmission of only the signal of a breath frequency component, may be used so that a noise component is not included to the detected signal of the ethanol gas concentration in breath also in the exemplary embodiment that makes use of the sensor using the oxide semiconductor. In this case, when the detected signal (second signal) of the vapor concentration, the oxygen concentration, or the carbon dioxide concentration, or both the the detect signal (first signal) of the ethanol gas concentration and the second signal are transmitted through the breath signal filter, the ethanol gas concentration may be detected based on the magnitude of the first signal to the second signal transmitted through the breath signal filter or on the magnitude of the first signal transmitted through the breath signal filter to the second signal transmitted through the breath signal filter.

Note that the expressions (25) and (27), which take the dilution magnification into consideration, may be applied to all the exemplary embodiments using the correction gas explained above. As a result, the ethanol concentration may be accurately detected when breath is diluted with the atmosphere and when breath directly comes into contact with the sensor without being diluted.

Figure 26:
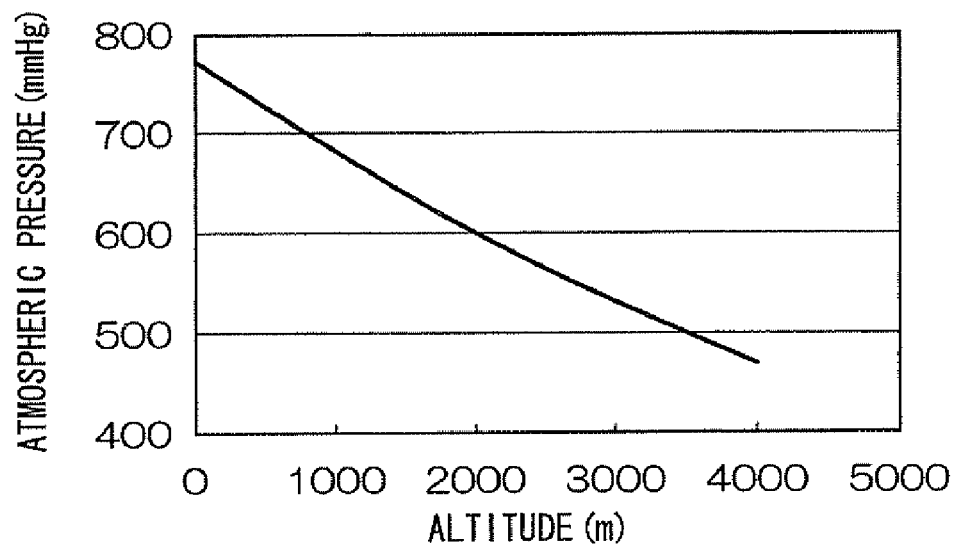
FIG. 26 is a graph showing the relation between an altitude and the atmospheric pressure.
Figure 27:
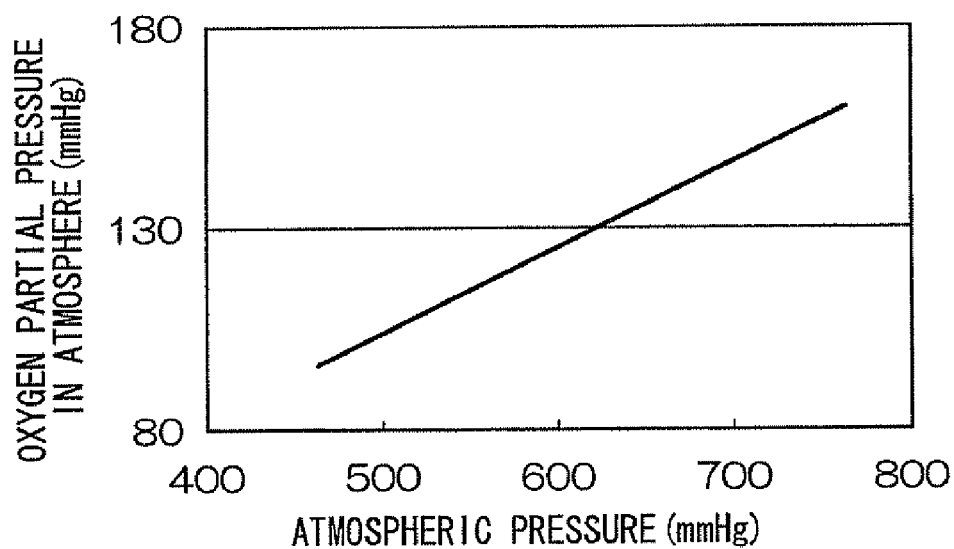
FIG. 27 is a graph showing the relation between the atmospheric pressure and the oxygen concentration (oxygen partial pressure) in the atmospheric pressure.

Next, a twelfth exemplary embodiment of the invention will be explained. As shown in FIG. 26, since the atmospheric pressure is low at a location having a high altitude, a pressure correction is necessary to accurately calculate an alcohol concentration. In general, when the pressure correction is necessary, it is performed by a pressure sensor. In the exemplary embodiment, an example, in which an oxygen sensor is used in place of the pressure sensor, will be explained paying attention to that the oxygen partial pressure in the atmosphere correlates with the atmospheric pressure as shown in FIG. 27 and the oxygen partial pressure in the atmosphere is lowered as the altitude becomes high and the atmospheric pressure becomes low.

Figure 28:
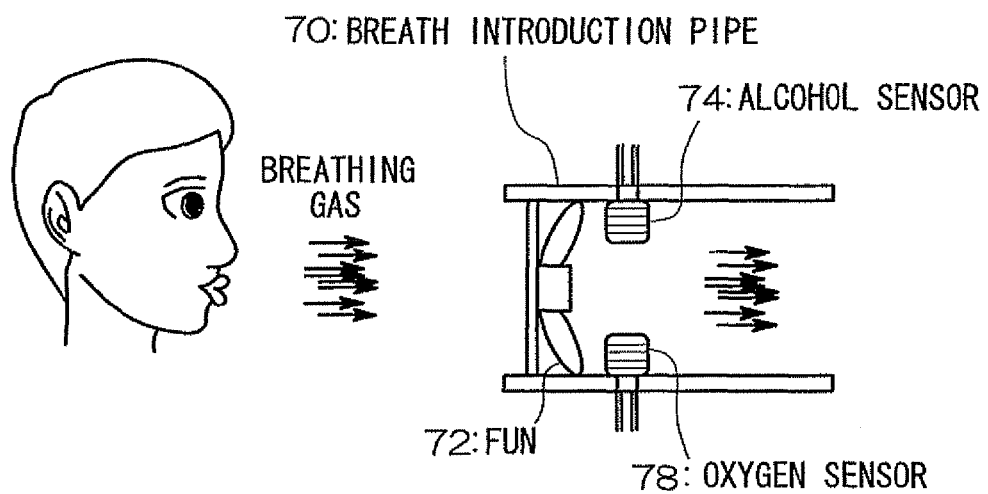
FIG. 28 is a schematic view showing a twelfth exemplary embodiment of the invention.

FIG. 28 is a schematic view showing an exemplary embodiment using a sensor employing an oxide semiconductor system. The sensor comprises a breath introduction pipe

70, a fan 72 attached to one end of the breath introduction pipe 70, and an alcohol sensor 74 and an oxygen sensor 78 which are disposed at mid-positions of the breath introduction pipe 70.

The fan 72 is used to effectively take breath into the breath introduction pipe 70 The breath exhausted from a person is sucked from one end of the breath introduction pipe 70 by the fan 72 and is exhausted from the other end of the breath introduction pipe 70 after it comes into contact with the alcohol sensor 74 and the oxygen sensor 78.

The alcohol sensor 74 is a sensor for detecting the ethanol component contained in air flowing in the breath introduction pipe 70, and, for example, TGS2620 (trade name, manufactured by Figaro Engineering Inc.) using an oxide tin semiconductor may be used.

The oxygen sensor 78 is a sensor for detecting oxygen flowing in the breath introduction pipe 70, and, for example, FCX-MVL (trade name, manufactured by Fujikura Ltd.) using a zirconia solid electrolyte may be used.

The breath exhausted from the person is mixed with air and arbitrarily diluted and reaches the alcohol sensor and the oxygen sensor.

Respective output ends of the alcohol sensor 74 and the oxygen sensor 78 are connected to an ethanol concentration determinator (not shown) which comprises a microcomputer and the like and is similar to that described above.

Figure 29:
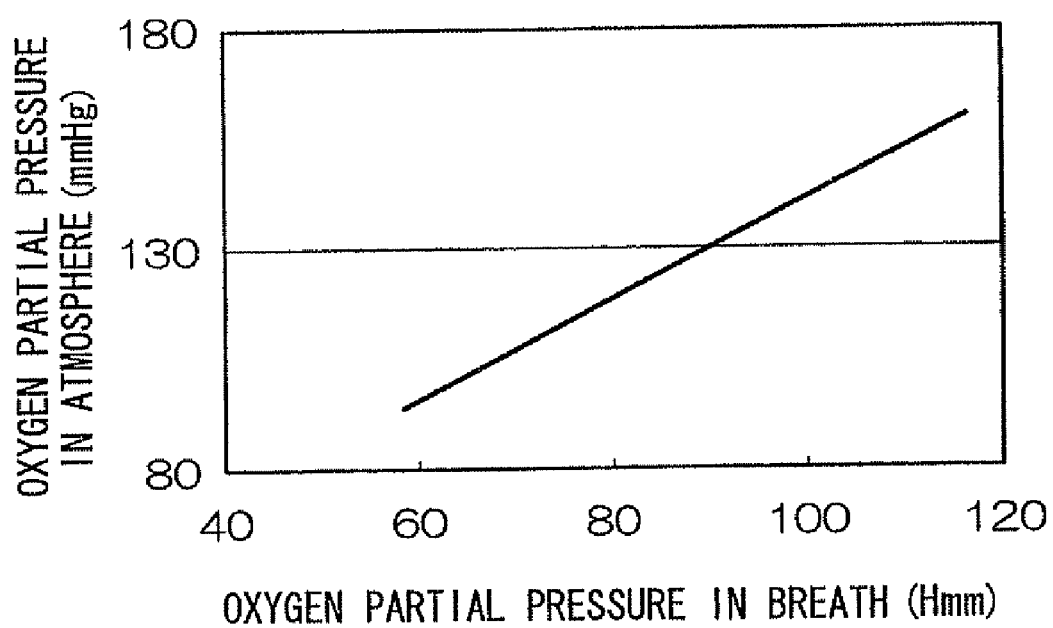
FIG. 29 is a graph showing the correlation between the oxygen concentration (oxygen partial pressure) in breath and the oxygen concentration (oxygen partial pressure) in the atmosphere.

The ethanol concentration determinator previously stores the correlation between the atmospheric pressure and the oxygen concentration in the atmosphere (oxygen partial pressure in the atmosphere), i.e., a table that defines the relation shown in FIG. 27 and the correlation between the oxygen concentration in the atmosphere (oxygen partial pressure in the atmosphere) and the oxygen concentration in breath (oxygen partial pressure in the atmosphere), i.e., a table that defines the relation shown in FIG. 29. Note that the correlations may be defined by expressions and stored in place of the tables.

The ethanol concentration determinator calculates the ethanol concentration in breath from the changes of the outputs from the sensors to the diluted breath according to a calculation formula shown below.

Further, in the exemplary embodiment, even if an altitude is high and the atmospheric pressure is lower than 1 atm (760 mmHg), the alcohol concentration in breath may be output by calculating the atmospheric pressure from the oxygen sensor and correcting the pressure. Note that, when the atmospheric pressure is not 1 atm, the oxygen concentration in breath is changed as the oxygen concentration in the atmosphere changes. However, since both of them have a correlation that the oxygen partial pressure in breath is increased as the oxygen partial pressure in the atmosphere increases as shown in FIG. 29, the ethanol concentration in breath may be calculated using the correlation.

$$[EtOH]breath = (([EtOH]peak - [EtOH]base) \times (breath\ dilution\ magnification) + [EtOH]base)/Pair \quad (28)$$

$$(breath\ dilution\ magnification) = ([O_2]breath - [O_2]base)/([O_2]peak - [O_2]base)$$

where, symbols in the expressions have the following meanings.

[EtOH]breath: the ethanol concentration in breath (after pressure is corrected),

[EtOH]base: the concentration output from an alcohol sensor before breath is introduced.

[EtOH]peak: the maximum value of the concentration output from the alcohol sensor when breath is introduced, (breath dilution magnification): magnification at which breath is diluted until it reaches a sensor, Pair: the atmospheric pressure calculated from the correlation between the atmospheric pressure and the oxygen concentration in the atmosphere ($[O_2]$base) (refer to FIG. 27), $[O_2]$breath: the oxygen concentration in breath, calculated from the correlation between the oxygen concentration in breath ($[O_2]$breath) and the oxygen concentration in the atmosphere ($[O_2]$base) (refer to FIG. 29), $[O_2]$base: the concentration output from an oxygen sensor before breath is introduced (the oxygen concentration in the atmosphere), and $[O_2]$peak: the maximum value of the concentration output from the oxygen sensor when breath is introduced.

Note that the maximum values are used as the valued output from the sensors (output concentrations) in the above explanation. However, the maximum values need not be necessarily used, and when a value, is output after the breath, which is introduced into the breath introduction pipe comes into contact with the alcohol sensor and the oxygen sensor, the ethanol gas concentration in breath may be calculated using the amount of change or the rate of change of the above output value likewise the above mentioned.

Although the example in which ethanol is detected from the breath of a driver is explained in the above exemplary embodiments, they may be also applied to a case in which ethanol is detected from the breath of a person other than a driver by arranging the ethanol concentration detector so that it can be carried.

Industrial Applicability

The invention can determine whether or not a person is in a drunk state by detecting the concentration of ethanol gas from breath of the person by mounting the ethanol concentration detector on a vehicle or by carrying it. When the ethanol concentration detector is mounted on the vehicle, it can be used to determine a drunk state when the vehicle is controlled so that a vehicle drive system is not driven in the drunk state.

The invention claimed is:

1. A gas detecting method comprising:
    detecting an intensity of an infrared light, which has a predetermined wavelength band including an absorption spectrum derived from a C—O stretching vibration of ethanol in an absorption spectrum generated by interaction with infrared light emitted from a face of a person as an infrared light absorption intensity of ethanol; and
    detecting the physical quantity relating to the concentration of ethanol gas contained in breath based on the magnitude of the detected infrared light absorption intensity of ethanol.

2. A gas detecting method comprising:
    detecting an intensity of an infrared light, which has a predetermined wavelength band including an absorption spectrum derived from a C—O stretching vibration of ethanol in an absorption spectrum generated by interaction with infrared light emitted from a face of a person as an infrared light absorption intensity of ethanol;
    detecting an intensity of an infrared light, which has a predetermined wavelength band including an absorption spectrum derived from a C—O stretching vibration of carbon dioxide in an absorption spectrum generated by interaction with infrared light emitted from the face of a person as an infrared light absorption intensity of carbon dioxide; and
    detecting a physical quantity relating to the concentration of ethanol gas contained in breath based on the detected infrared light absorption intensity of carbon dioxide and the detected infrared light absorption intensity of ethanol.

3. A gas detecting method comprising:

detecting an intensity of an infrared light, which has a predetermined wavelength band including an absorption spectrum derived from a C—O stretching vibration of ethanol in an absorption spectrum generated by interaction with infrared light emitted from a face of a person as an infrared light absorption intensity of ethanol;

detecting an intensity of an infrared light, which has a predetermined wavelength band including an absorption spectrum of vapor in an absorption spectrum generated by interaction with infrared light emitted from the face of the person as an infrared light absorption intensity of vapor; and detecting a physical quantity relating to the concentration of ethanol gas contained in breath is detected based on the detected infrared light absorption intensity of vapor and the detected infrared light absorption intensity of ethanol.

4. A gas detecting apparatus comprising:

an optical filter for ethanol that allows to transmit an infrared light having a predetermined wavelength band including an absorption spectrum derived from a C—O stretching vibration of ethanol in an absorption spectrum generated by interaction with infrared light emitted from a face of a person;

a converting component for ethanol that converts the infrared light transmitted through the optical filter for ethanol to an electric signal; and detecting component for detecting the physical quantity relating to the concentration of ethanol gas contained in breath based on the magnitude of the electric signal converted by the converting component for ethanol.

5. The gas detecting apparatus of claim 4, wherein the detecting component detects the physical quantity [EtOH] relating to the concentration of ethanol gas according to the following expression $$[EtOH] = -\ln(Te/To)/ke \times L \ldots \quad (6)$$

where, Te shows the amount of transmitted infrared light obtained from the electric signal converted by the converting component for ethanol, To shows the amount of infrared light emitted from the face of a person, ke shows an absorption coefficient of ethanol gas, L shows the interacting length between ethanol gas and the infrared light emitted from the face of the person, and ln shows natural logarithm.

6. The gas detecting apparatus of claim 4, further comprising a breath filter that allows to transmits a signal having a breath frequency component from the electric signal converted by the converting component for ethanol, wherein the detecting component detects the physical quantity relating to the concentration of ethanol gas based on the magnitude of the electric signal converted by the converting component for ethanol and transmitted through the breath filter.

7. A gas detecting apparatus comprising:

an optical filter for ethanol that allows to transmit an infrared light having a predetermined wavelength band including an absorption spectrum derived from a C—O stretching vibration of ethanol in an absorption spectrum generated by interaction with infrared light emitted from the face of a person;

an optical filter for reference that transmits the infrared light having the wavelength band of the infrared light emitted from the face of the person and having a band other than the predetermined wavelength band;

a converting component for ethanol that converts the infrared light transmitted through the optical filter for ethanol to an electric signal;

a converting component for reference that converts the infrared light transmitted through the optical filter for reference to an electric signal; and a detecting component that detects the physical quantity relating to the concentration of ethanol gas contained in breath based on the electric signals converted by the converting component for ethanol and the converting component for reference.

8. The gas detecting apparatus of claim 7, wherein the detecting component detects the physical quantity [EtOH] relating to the concentration of ethanol gas according to the following expression $$[EtOH] = -\ln(Te/To)/ke \times L \ldots \quad (7)$$

where, Te shows the amount of transmitted infrared light obtained from the electric signal converted by the converting component for ethanol, To shows the amount of transmitted infrared light emitted from the face of a person obtained by the electric signal converted by the converting component for reference, ke shows an absorption coefficient of ethanol gas, L shows the interacting length between ethanol gas and the infrared light emitted from the face of the person, and ln shows natural logarithm.

9. A gas detecting apparatus comprising:

an optical filter for ethanol that allows to transmit an infrared light having a predetermined wavelength band including an absorption spectrum derived from a C—O stretching vibration of ethanol in an absorption spectrum generated by interaction with infrared light emitted from a face of a person;

an optical filter for carbon dioxide that allows to transmit an infrared light having a predetermined wavelength band including an absorption spectrum derived from a C—O stretching vibration of carbon dioxide in an absorption spectrum generated by interaction with infrared light emitted from the face of the person;

a converting component for ethanol that converts the infrared light transmitted through the optical filter for ethanol to an electric signal;

a converting component for carbon dioxide that converts the infrared light transmitted through the optical filter for carbon dioxide to an electric signal; and a detecting component that detects the physical quantity relating to the concentration of ethanol gas contained in breath based on the electric signals converted by the converting component for carbon dioxide and the converting component for ethanol.

10. The gas detecting apparatus of claim 9, wherein the detecting component detects the physical quantity [EtOH] relating to the concentration of ethanol gas according to the following expression $$[EtOH] = (ne(t_2) - ne(t_1))/(nc(t_2) - nc(t_1)) \ldots \quad (8)$$

where, $ne(t_2)$, $ne(t_1)$ show the physical quantities relating to the concentration of ethanol gas shown by ne of the following expression at times $t_2$, $t_1$, and $nc(t_2)$, $nc(t_1)$ show the physical quantities relating to the concentration of carbon dioxide shown by nc of the following expression at the times $t_2$, $t_1$ $$ne = -ln(Te/To)/ke \times L$$

$$nc = -ln(Tc/To)/kc \times L$$

where, Te shows the amount of transmitted infrared light obtained from the electric signal converted by the converting component for ethanol, Tc shows the amount of transmitted infrared light obtained from the electric signal converted by the converting component for carbon dioxide, To shows the amount of infrared light emitted from the face of a person, ke shows an absorption coefficient of ethanol gas, kc shows an absorption coefficient of carbon dioxide and L shows the interacting length between ethanol gas and carbon dioxide and the infrared light emitted from the face of the person.

11. The gas detecting apparatus of claim 9, further comprising:
an optical filter for reference that transmits the infrared light having the wavelength band of infrared light emitted from the face of a person and having a wavelength band other than the predetermined wavelength band; and
a converting component for reference that converts the infrared light transmitted through the optical filter for reference to an electric signal,
wherein the detecting component detects the physical quantity relating to the concentration of ethanol gas further using the electric signal converted by the converting component for reference.

12. The gas detecting apparatus of claim 9, further comprising:
an optical filter for reference that transmits the infrared light having the wavelength band of the infrared light emitted from the face of a person and having a band other than the predetermined wavelength band; and
a converting component for reference that converts the infrared light transmitted through the optical filter for reference to an electric signal,
wherein the detecting component detects the physical quantity [EtOH] relating to the concentration of ethanol gas using the amount of transmitted infrared light emitted from the face of the person obtained by the electric signal converted by the converting component for reference as the amount of infrared light To emitted from the face of the person.

13. The gas detecting apparatus of claim 9, further comprising a breath filter for allowing the transmission of a signal having a breath frequency component from the electric signal converted by the converting component for ethanol and the electric signal converted by the converting component for carbon dioxide, wherein the detecting component detects the physical quantity relating to the concentration of ethanol gas based on the magnitudes of the electric signals converted by the converting component for ethanol and the converting component for carbon dioxide and transmitted through the breath filter.

14. A gas detecting apparatus comprising:
an optical filter for ethanol that allows to transmit an infrared light having a predetermined wavelength band including an absorption spectrum derived from a C—O stretching vibration of ethanol in an absorption spectrum generated by interaction with infrared light emitted from a face of a person;
an optical filter for vapor that allows to transmit an infrared light having a predetermined wavelength band including an absorption spectrum of vapor in an absorption spectrum generated by interaction with infrared light emitted from the face of a person;
a converting component for ethanol that converts the infrared light transmitted through the optical filter for ethanol to an electric signal;
a converting component for vapor that converts the infrared light transmitted through the optical filter for vapor to an electric signal; and
a detecting component that detects the physical quantity relating to the concentration of ethanol gas contained in breath based on the electric signals converted by the converting component for vapor and the converting component for ethanol.

15. The gas detecting apparatus of claim 14, wherein the detecting component detects the physical quantity [EtOH] relating to the concentration of ethanol gas according to the following expression $$[EtOH] = (ne(t_2) - ne(t_1))/(nw(t_2) - nw(t_1)) \ldots \quad (9)$$

where, $ne(t_2)$, $ne(t_1)$ show the physical quantities relating to the concentration of ethanol gas shown by ne of the following expression at times $t_2$, $t_1$, and $nw(t_2)$, $nw(t_1)$ show the physical quantity relating to the concentration of vapor shown by nw of the following expression at the times $t_2$, $t_0$ $$ne = -ln(Te/To)/ke \times L$$

$$nw = -ln(Tw/To)/kw \times L$$

where, Te shows the amount of transmitted infrared light obtained from the electric signal converted by the converting component for ethanol, Tw shows the amount of transmitted infrared light obtained from the electric signal converted by the converting component for vapor, To shows the amount of infrared light emitted from the face of a person, ke shows an absorption coefficient of ethanol, kw shows an absorption coefficient of vapor, and L shows the interacting length between ethanol gas and vapor and the infrared light emitted from the face of the person.

16. The gas detecting apparatus of claim 14, further comprising a breath filter for allowing the transmission of a signal having a breath frequency component from the electric signal converted by the converting component for ethanol and the electric signal converted by the converting component for vapor, wherein the detecting component detects the physical quantity relating to the concentration of ethanol gas based on the magnitudes of the electric signals converted by the converting component for ethanol and the converting component for vapor and transmitted through the breath filter.

* * * * *